United States Patent
Srivastava et al.

(10) Patent No.: US 12,201,838 B2
(45) Date of Patent: *Jan. 21, 2025

(54) PAIN MANAGEMENT BASED ON EMOTIONAL EXPRESSION MEASUREMENTS

(71) Applicant: Boston Scientific Neuromodulation Corporation, Valencia, CA (US)

(72) Inventors: Kyle Harish Srivastava, Saint Paul, MN (US); Bryan Allen Clark, Forest Lake, MN (US); Elizabeth Mary Annoni, White Bear Lake, MN (US); Sandra Nagale, Bolton, MA (US); Pramodsingh Hirasingh Thakur, Woodbury, MN (US); Jianwen Gu, Valencia, CA (US); David L. Perschbacher, Blaine, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 18/085,270

(22) Filed: Dec. 20, 2022

(65) Prior Publication Data
US 2023/0120858 A1 Apr. 20, 2023

Related U.S. Application Data

(63) Continuation of application No. 17/145,514, filed on Jan. 11, 2021, now Pat. No. 11,571,577, which is a (Continued)

(51) Int. Cl.
*A61N 1/36* (2006.01)
*A61B 5/00* (2006.01)
(Continued)

(52) U.S. Cl.
CPC ........ *A61N 1/36139* (2013.01); *A61B 5/0077* (2013.01); *A61B 5/1104* (2013.01);
(Continued)

(58) Field of Classification Search
CPC .................................................. A61N 1/36071
See application file for complete search history.

(56) References Cited

U.S. PATENT DOCUMENTS

| | | | |
|---|---|---|---|
| 4,297,685 A | 10/1981 | Brainard, II | |
| 5,187,675 A | 2/1993 | Dent et al. | |

(Continued)

FOREIGN PATENT DOCUMENTS

| | | | |
|---|---|---|---|
| AU | 2017335497 B2 | 4/2020 | |
| AU | 2017334841 B2 | 7/2020 | |

(Continued)

OTHER PUBLICATIONS

"2015 Sleep in America® Poll Sleep and Pain—Summary of Findings", National Sleep Foundation, (2015), 1-54.
(Continued)

*Primary Examiner* — Alyssa M Alter
(74) *Attorney, Agent, or Firm* — Schwegman Lundberg & Woessner, P.A.

(57) ABSTRACT

This document discusses, among other things, systems and methods for managing pain in a subject. A system may include one or more sensors configured to sense from the subject information corresponding to emotional reaction to pain, such as emotional expression. The emotional expression includes facial or vocal expression. A pain analyzer circuit may generate a pain score using signal metrics of facial or vocal expression extracted from the sensed information. The pain score may be output to a user or a process. The system may additionally include a neurostimulator that can adaptively control the delivery of pain therapy by
(Continued)

automatically adjusting stimulation parameters based on the pain score.

20 Claims, 4 Drawing Sheets

Related U.S. Application Data continuation of application No. 15/867,873, filed on Jan. 11, 2018, now Pat. No. 10,926,091.

(60) Provisional application No. 62/445,082, filed on Jan. 11, 2017.

(51) Int. Cl.
| | | |
|---|---|---|
| *A61B 5/11* | (2006.01) | |
| *A61B 5/16* | (2006.01) | |
| *A61N 1/05* | (2006.01) | |
| *G16H 20/70* | (2018.01) | |
| *G16H 40/63* | (2018.01) | |
| *G16H 50/30* | (2018.01) | |

(52) U.S. Cl.
CPC ............ *A61B 5/165* (2013.01); *A61B 5/4803* (2013.01); *A61B 5/4824* (2013.01); *A61B 5/4836* (2013.01); *A61B 5/4848* (2013.01); *A61N 1/0534* (2013.01); *A61N 1/0551* (2013.01); *A61N 1/36062* (2017.08); *A61N 1/36071* (2013.01); *G16H 20/70* (2018.01); *G16H 40/63* (2018.01); *G16H 50/30* (2018.01)

(56) References Cited

U.S. PATENT DOCUMENTS

| | | | |
|---|---|---|---|
| 5,774,591 | A | 6/1998 | Black et al. |
| 6,016,103 | A | 1/2000 | Leavitt |
| 6,076,011 | A | 6/2000 | Hoover |
| 6,088,040 | A | 7/2000 | Oda et al. |
| 6,173,260 | B1 | 1/2001 | Slaney |
| 6,480,734 | B1 | 11/2002 | Zhang et al. |
| 6,497,658 | B2 | 12/2002 | Roizen et al. |
| 6,654,632 | B2 | 11/2003 | Lange et al. |
| 6,659,968 | B1 | 12/2003 | McClure |
| 6,731,984 | B2 | 5/2004 | Cho et al. |
| 6,871,099 | B1 | 3/2005 | Whitehurst et al. |
| 7,001,337 | B2 | 2/2006 | Dekker |
| 7,004,907 | B2 | 2/2006 | Banet et al. |
| 7,177,686 | B1 | 2/2007 | Turcott |
| 7,189,204 | B2 | 3/2007 | Ni et al. |
| 7,222,075 | B2 | 5/2007 | Petrushin |
| 7,299,086 | B2 | 11/2007 | McCabe et al. |
| 7,376,457 | B2 | 5/2008 | Ross |
| 7,407,485 | B2 | 8/2008 | Huiku |
| 7,463,927 | B1 | 12/2008 | Chaouat |
| 7,566,308 | B2 | 7/2009 | Stahmann |
| 7,627,475 | B2 | 12/2009 | Petrushin |
| 7,636,602 | B2 | 12/2009 | Baru Fassio et al. |
| 7,650,184 | B2 | 1/2010 | Walter |
| 7,678,061 | B2 | 3/2010 | Lee et al. |
| 7,775,993 | B2 | 8/2010 | Heruth et al. |
| 7,957,809 | B2 | 6/2011 | Bourget et al. |
| 7,986,991 | B2 | 7/2011 | Prichep |
| 8,019,439 | B2 | 9/2011 | Kuzma et al. |
| 8,055,348 | B2 | 11/2011 | Heruth et al. |
| 8,083,682 | B2 | 12/2011 | Dalal et al. |
| 8,192,376 | B2 | 6/2012 | Lovett et al. |
| 8,209,182 | B2 | 6/2012 | Narayanan |
| 8,290,596 | B2 | 10/2012 | Wei et al. |
| 8,332,038 | B2 | 12/2012 | Heruth et al. |
| 8,398,556 | B2 | 3/2013 | Sethi et al. |
| 8,447,401 | B2 | 5/2013 | Miesel et al. |
| 8,475,370 | B2 | 7/2013 | McCombie et al. |
| 8,529,459 | B2 | 9/2013 | Malker et al. |
| 8,606,356 | B2 | 12/2013 | Lee et al. |
| 8,688,221 | B2 | 4/2014 | Miesel |
| 8,744,587 | B2 | 6/2014 | Miesel et al. |
| 8,805,518 | B2 | 8/2014 | King et al. |
| 9,066,659 | B2 | 6/2015 | Thakur et al. |
| 9,072,870 | B2 | 7/2015 | Wu et al. |
| 9,119,965 | B2 | 9/2015 | Xi et al. |
| 9,314,168 | B2 | 4/2016 | Watson et al. |
| 9,395,792 | B1 | 7/2016 | Kahn et al. |
| 9,517,344 | B1 | 12/2016 | Bradley |
| 10,349,212 | B2 | 7/2019 | Tartz et al. |
| 10,610,688 | B2 | 4/2020 | Thakur et al. |
| 10,631,776 | B2 | 4/2020 | Annoni et al. |
| 10,631,777 | B2 | 4/2020 | Clark et al. |
| 10,667,747 | B2 | 6/2020 | Annoni et al. |
| 10,675,469 | B2 | 6/2020 | Annoni et al. |
| 10,729,905 | B2 | 8/2020 | Annoni et al. |
| 10,750,994 | B2 * | 8/2020 | Annoni ................ A61B 5/4836 |
| 10,898,718 | B2 | 1/2021 | Srivastava et al. |
| 10,926,091 | B2 * | 2/2021 | Srivastava ......... A61N 1/36071 |
| 10,960,210 | B2 | 3/2021 | Srivastava et al. |
| 11,089,997 | B2 | 8/2021 | Annoni et al. |
| 11,337,646 | B2 | 5/2022 | Annoni et al. |
| 11,395,625 | B2 | 7/2022 | Clark et al. |
| 11,439,827 | B2 | 9/2022 | Srivastava et al. |
| 11,446,499 | B2 | 9/2022 | Thakur et al. |
| 11,541,240 | B2 | 1/2023 | Annoni et al. |
| 11,571,577 | B2 * | 2/2023 | Srivastava ............. G16H 40/63 |
| 11,751,804 | B2 | 9/2023 | Annoni et al. |
| 11,857,794 | B2 | 1/2024 | Annoni et al. |
| 11,883,664 | B2 | 1/2024 | Thakur et al. |
| 2001/0037222 | A1 | 11/2001 | Platt et al. |
| 2002/0042563 | A1 | 4/2002 | Becerra et al. |
| 2004/0015091 | A1 | 1/2004 | Greenwald et al. |
| 2005/0010262 | A1 | 1/2005 | Sharan et al. |
| 2005/0209643 | A1 | 9/2005 | Heruth et al. |
| 2007/0167859 | A1 | 7/2007 | Finneran et al. |
| 2007/0213783 | A1 | 9/2007 | Pless |
| 2007/0260285 | A1 | 11/2007 | Libbus et al. |
| 2008/0015659 | A1 | 1/2008 | Zhang et al. |
| 2008/0077192 | A1 | 3/2008 | Harry et al. |
| 2008/0177191 | A1 | 7/2008 | Patangay et al. |
| 2008/0249430 | A1 | 10/2008 | John et al. |
| 2009/0124863 | A1 | 5/2009 | Liu et al. |
| 2009/0192556 | A1 | 7/2009 | Wu et al. |
| 2009/0312663 | A1 | 12/2009 | John et al. |
| 2009/0318986 | A1 | 12/2009 | Alo et al. |
| 2010/0016913 | A1 | 1/2010 | Arcot-Krishnamurthy et al. |
| 2010/0105997 | A1 | 4/2010 | Ecker et al. |
| 2010/0191311 | A1 | 7/2010 | Scheiner et al. |
| 2010/0286549 | A1 | 11/2010 | John et al. |
| 2011/0015702 | A1 | 1/2011 | Ternes et al. |
| 2011/0021928 | A1 | 1/2011 | Giovangrandi et al. |
| 2011/0034760 | A1 | 2/2011 | Brynelsen et al. |
| 2011/0112420 | A1 | 5/2011 | Nagata et al. |
| 2011/0124979 | A1 | 5/2011 | Heneghan et al. |
| 2011/0137134 | A1 | 6/2011 | Hemmerling et al. |
| 2011/0172562 | A1 | 7/2011 | Sahasrabudhe et al. |
| 2011/0224749 | A1 | 9/2011 | Ben-David et al. |
| 2011/0306846 | A1 | 12/2011 | Osorio |
| 2012/0046715 | A1 | 2/2012 | Moffitt et al. |
| 2012/0109012 | A1 | 5/2012 | Cinbis |
| 2012/0123223 | A1 | 5/2012 | Freeman et al. |
| 2012/0150545 | A1 | 6/2012 | Simon |
| 2012/0277818 | A1 | 11/2012 | Stancer et al. |
| 2013/0066394 | A1 | 3/2013 | Saab |
| 2013/0165994 | A1 | 6/2013 | Ternes et al. |
| 2013/0211291 | A1 | 8/2013 | Tran |
| 2013/0268016 | A1 | 10/2013 | Xi et al. |
| 2014/0276188 | A1 | 9/2014 | Jardin |
| 2014/0276549 | A1 | 9/2014 | Osorio |
| 2014/0309709 | A1 | 10/2014 | Gozani et al. |
| 2015/0005842 | A1 | 1/2015 | Lee et al. |
| 2015/0025335 | A1 | 1/2015 | Jain et al. |
| 2015/0148878 | A1 | 5/2015 | Yoo et al. |
| 2015/0289803 | A1 | 10/2015 | Wu et al. |
| 2016/0022203 | A1 | 1/2016 | Arnold et al. |
| 2016/0082265 | A1 | 3/2016 | Moffitt et al. |
| 2016/0129272 | A1 | 5/2016 | Hou et al. |

(56) References Cited

U.S. PATENT DOCUMENTS

| | | |
|---|---|---|
| 2016/0144194 A1 | 5/2016 | Roothans et al. |
| 2016/0158551 A1 | 6/2016 | Kent et al. |
| 2016/0198996 A1 | 7/2016 | Dullen |
| 2016/0243359 A1 | 8/2016 | Sharma |
| 2016/0302720 A1 | 10/2016 | John et al. |
| 2016/0350509 A1 | 12/2016 | Sharma |
| 2016/0361515 A1 | 12/2016 | Jung et al. |
| 2016/0374567 A1 | 12/2016 | Breslow et al. |
| 2017/0128722 A1 | 5/2017 | Perez |
| 2017/0136264 A1 | 5/2017 | Hyde et al. |
| 2017/0164876 A1 | 6/2017 | Hyde et al. |
| 2017/0165485 A1 | 6/2017 | Sullivan et al. |
| 2018/0078768 A1 | 3/2018 | Thakur et al. |
| 2018/0085055 A1 | 3/2018 | Annoni et al. |
| 2018/0085584 A1 | 3/2018 | Thakur et al. |
| 2018/0110464 A1 | 4/2018 | Annoni et al. |
| 2018/0126169 A1 | 5/2018 | Hou et al. |
| 2018/0192941 A1 | 7/2018 | Annoni et al. |
| 2018/0192942 A1 | 7/2018 | Clark et al. |
| 2018/0192943 A1 | 7/2018 | Annoni et al. |
| 2018/0193644 A1 | 7/2018 | Annoni et al. |
| 2018/0193650 A1 | 7/2018 | Srivastava et al. |
| 2018/0193651 A1 | 7/2018 | Annoni et al. |
| 2018/0193652 A1 | 7/2018 | Srivastava et al. |
| 2018/0229040 A1 | 8/2018 | Srivastava et al. |
| 2019/0022397 A1 | 1/2019 | Srivastava et al. |
| 2020/0188673 A1 | 6/2020 | Thakur et al. |
| 2020/0214623 A1 | 7/2020 | Annoni et al. |
| 2020/0214624 A1 | 7/2020 | Clark et al. |
| 2020/0238087 A1 | 7/2020 | Annoni et al. |
| 2020/0359960 A1 | 11/2020 | Annoni et al. |
| 2021/0060343 A1 | 3/2021 | Srivastava et al. |
| 2021/0128921 A1 | 5/2021 | Srivastava et al. |
| 2021/0178164 A1 | 6/2021 | Srivastava et al. |
| 2021/0345950 A1 | 11/2021 | Annoni et al. |
| 2022/0323760 A1 | 10/2022 | Thakur et al. |
| 2022/0379119 A1 | 12/2022 | Srivastava et al. |
| 2023/0103448 A1 | 4/2023 | Annoni et al. |

FOREIGN PATENT DOCUMENTS

| | | |
|---|---|---|
| EP | 1059064 A2 | 12/2000 |
| EP | 1897586 A1 | 3/2008 |
| EP | 3519037 B1 | 7/2020 |
| EP | 3568069 B1 | 4/2021 |
| EP | 3518736 B1 | 8/2021 |
| KR | 20050053824 A | 6/2005 |
| KR | 1020050053824 A | 6/2005 |
| RU | 2559783 C1 | 8/2015 |
| WO | WO-2007007058 A1 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2014151860 A1 | 9/2014 |
| WO | WO-2015060888 A1 | 4/2015 |
| WO | WO-2015128567 | 9/2015 |
| WO | WO-2016025989 A1 | 2/2016 |
| WO | WO-2016077786 A1 | 5/2016 |
| WO | WO-2018052695 A1 | 3/2018 |
| WO | WO-2018063637 A1 | 4/2018 |
| WO | WO-2018063912 A1 | 4/2018 |
| WO | WO-2018080887 A1 | 5/2018 |
| WO | WO-2019018206 A1 | 1/2019 |

OTHER PUBLICATIONS

"U.S. Appl. No. 15/687,925, Final Office Action mailed Feb. 14, 2019", 10 pgs.

"U.S. Appl. No. 15/687,925, Non Final Office Action mailed Jun. 11, 2019", 11 pgs.

"U.S. Appl. No. 15/687,925, Non Final Office Action mailed Oct. 9, 2018", 9 pgs.

"U.S. Appl. No. 15/687,925, Response filed Jan. 9, 2019 to Non Final Office Action mailed Oct. 9, 2018", 9 pgs.

"U.S. Appl. No. 15/687,925, Response filed May 13, 2019 to Final Office Action mailed Feb. 14, 2019", 11 pgs.

"U.S. Appl. No. 15/688,676, Examiner Interview Summary mailed Sep. 25, 2019", 3 pgs.

"U.S. Appl. No. 15/688,676, Final Office Action mailed Jul. 29, 2019", 7 pgs.

"U.S. Appl. No. 15/688,676, Non Final Office Action mailed Jan. 11, 2019", 7 pgs.

"U.S. Appl. No. 15/688,676, Non Final Office Action mailed Oct. 30, 2019", 6 pgs.

"U.S. Appl. No. 15/688,676, Notice of Allowance mailed Apr. 14, 2020", 7 pgs.

"U.S. Appl. No. 15/688,676, Response filed Jan. 7, 2020 to Non Final Office Action mailed Oct. 30, 2019", 10 pgs.

"U.S. Appl. No. 15/688,676, Response filed Sep. 25, 2019 to Final Office Action mailed Jul. 29, 2019", 10 pgs.

"U.S. Appl. No. 15/688,676, Response filed Apr. 9, 2019 to Non Final Office Action mailed Jan. 11, 2019", 12 pgs.

"U.S. Appl. No. 15/711,578, Examiner Interview Summary mailed Aug. 28, 2019", 3 pgs.

"U.S. Appl. No. 15/711,578, Non Final Office Action mailed May 23, 2019", 6 pgs.

"U.S. Appl. No. 15/711,578, Notice of Allowance mailed Nov. 25, 2019", 7 pgs.

"U.S. Appl. No. 15/711,578, Repsonse filed Aug. 23, 2019 to Non Final Office Action mailed May 23, 2019", 11 pgs.

"U.S. Appl. No. 15/711,578, Supplemental Response filed Aug. 28, 2019 to Non Final Office Action mailed May 23, 2019", 11 pgs.

"U.S. Appl. No. 15/788,403, 312 Amendment filed Apr. 22, 2020", 8 pgs.

"U.S. Appl. No. 15/788,403, Corrected Notice of Allowability mailed Mar. 18, 2020", 2 pgs.

"U.S. Appl. No. 15/788,403, Non Final Office Action mailed Jul. 23, 2019", 9 pgs.

"U.S. Appl. No. 15/788,403, Notice of Allowance mailed Jan. 23, 2020", 7 pgs.

"U.S. Appl. No. 15/788,403, PTO Response to Rule 312 Communication mailed Apr. 30, 2020", 2 pgs.

"U.S. Appl. No. 15/788,403, Response filed Oct. 8, 2019 to Non Final Office Action mailed Jul. 23, 2019", 11 pgs.

"U.S. Appl. No. 15/867,756, Examiner Interview Summary mailed Aug. 28, 2019", 3 pgs.

"U.S. Appl. No. 15/867,756, Non Final Office Action mailed Jul. 1, 2019", 8 pgs.

"U.S. Appl. No. 15/867,756, Notice of Allowance mailed Dec. 19, 2019", 7 pgs.

"U.S. Appl. No. 15/867,756, Response filed Aug. 29, 2019 to Non Final Office Action mailed Jul. 1, 2019", 11 pgs.

"U.S. Appl. No. 15/867,760, Examiner Interview Summary mailed Aug. 28, 2019", 3 pgs.

"U.S. Appl. No. 15/867,760, Non Final Office Action mailed Jul. 1, 2019", 8 pgs.

"U.S. Appl. No. 15/867,760, Notice of Allowance mailed Dec. 19, 2019", 7 pgs.

"U.S. Appl. No. 15/867,760, Response filed Aug. 29, 2019 to Non-Final Office Action mailed Jul. 1, 2019", 11 pgs.

"U.S. Appl. No. 15/867,767, Non Final Office Action mailed Dec. 17, 2019", 11 pgs.

"U.S. Appl. No. 15/867,767, Notice of Allowance mailed Apr. 6, 2020", 5 pgs.

"U.S. Appl. No. 15/867,767, Response filed Mar. 4, 2020 to Non Final Office Action mailed Dec. 17, 2019", 10 pgs.

"U.S. Appl. No. 15/867,772, Advisory Action mailed Dec. 22, 2020", 3 pgs.

"U.S. Appl. No. 15/867,772, Examiner Interview Summary mailed Apr. 29, 2021", 2 pgs.

"U.S. Appl. No. 15/867,772, Examiner Interview Summary mailed Dec. 11, 2020", 2 pgs.

"U.S. Appl. No. 15/867,772, Final Office Action mailed Oct. 22, 2020", 10 pgs.

(56) References Cited

OTHER PUBLICATIONS

"U.S. Appl. No. 15/867,772, Non Final Office Action mailed Apr. 2, 2020", 9 pgs.
"U.S. Appl. No. 15/867,772, Notice of Allowance mailed Apr. 23, 2021", 5 pgs.
"U.S. Appl. No. 15/867,772, PTO Response to Rule 312 Communication mailed Dec. 22, 2020", 4 pgs.
"U.S. Appl. No. 15/867,772, Response filed Jun. 30, 2020 to Non Final Office Action mailed Apr. 2, 2020", 10 pgs.
"U.S. Appl. No. 15/867,772, Response filed Dec. 15, 2020 to Final Office Action mailed Oct. 22, 2020", 12 pgs.
"U.S. Appl. No. 15/867,789, Non Final Office Action mailed Apr. 2, 2020", 10 pgs.
"U.S. Appl. No. 15/867,801, Non Final Office Action mailed Sep. 30, 2019", 10 pgs.
"U.S. Appl. No. 15/867,801, Notice of Allowance mailed Feb. 5, 2020", 8 pgs.
"U.S. Appl. No. 15/867,801, Response filed Dec. 18, 2019 to Non Final Office Action mailed Sep. 30, 2019", 12 pgs.
"U.S. Appl. No. 15/867,873, Non Final Office Action mailed Apr. 3, 2020", 11 pgs.
"U.S. Appl. No. 15/867,873, Notice of Allowance mailed Oct. 22, 2020", 5 pgs.
"U.S. Appl. No. 15/867,873, Response filed Jun. 30, 2020 to Non Final Office Action mailed Apr. 1, 2020", 10 pgs.
"U.S. Appl. No. 15/888,808, Advisory Action mailed Feb. 10, 2020", 2 pgs.
"U.S. Appl. No. 15/888,808, Examiner Interview Summary mailed Aug. 3, 2020", 3 pgs.
"U.S. Appl. No. 15/888,808, Examiner Interview Summary mailed Nov. 21, 2019", 3 pgs.
"U.S. Appl. No. 15/888,808, Final Office Action mailed Dec. 16, 2019", 7 pgs.
"U.S. Appl. No. 15/888,808, Non Final Office Action mailed Jul. 2, 2020", 11 pgs.
"U.S. Appl. No. 15/888,808, Non Final Office Action mailed Sep. 11, 2019", 7 pgs.
"U.S. Appl. No. 15/888,808, Notice of Allowance mailed Nov. 30, 2020", 9 pgs.
"U.S. Appl. No. 15/888,808, Response filed Jan. 31, 2020 to Final Office Action mailed Dec. 16, 2019", 11 pgs.
"U.S. Appl. No. 15/888,808, Response filed Mar. 16, 2020 to Advisory Action mailed Feb. 10, 2020", 8 pgs.
"U.S. Appl. No. 15/888,808, Response filed Sep. 29, 2020 to Non Final Office Action mailed Jul. 2, 2020", 11 pgs.
"U.S. Appl. No. 15/888,808, Response filed Nov. 19, 2019 to Non Final Office Action mailed Sep. 11, 2019", 10 pgs.
"U.S. Appl. No. 16/034,304, Examiner Interview Summary mailed Sep. 15, 2020", 3 pgs.
"U.S. Appl. No. 16/034,304, Final Office Action mailed Jul. 27, 2020", 11 pgs.
"U.S. Appl. No. 16/034,304, Non Final Office Action mailed Apr. 3, 2020", 15 pgs.
"U.S. Appl. No. 16/034,304, Notice of Allowance mailed Sep. 29, 2020", 8 pgs.
"U.S. Appl. No. 16/034,304, Response filed Jun. 30, 2020 to Non Final Office Action mailed Apr. 3, 2020", 13 pgs.
"U.S. Appl. No. 16/034,304, Response filed Sep. 16, 2020 to Final Office Action mailed Jul. 27, 2020", 11 pgs.
"U.S. Appl. No. 16/800,822, Non Final Office Action mailed Nov. 29, 2021", 5 pgs.
"U.S. Appl. No. 16/800,822, Notice of Allowance mailed May 18, 2022", 7 pgs.
"U.S. Appl. No. 16/800,822, Response filed Feb. 3, 2022 to Non Final Office Action mailed Nov. 29, 2021", 7 pgs.
"U.S. Appl. No. 16/820,474, Corrected Notice of Allowability mailed Feb. 9, 2022", 2 pgs.
"U.S. Appl. No. 16/820,474, Non Final Office Action mailed Oct. 12, 2021", 7 pgs.
"U.S. Appl. No. 16/820,474, Notice of Allowance mailed Jan. 25, 2022", 7 pgs.
"U.S. Appl. No. 16/820,474, Response filed Dec. 16, 2021 to Non Final Office Action mailed Oct. 12, 2021", 9 pgs.
"U.S. Appl. No. 16/821,161, Non Final Office Action mailed Jan. 3, 2022", 5 pgs.
"U.S. Appl. No. 16/821,161, Notice of Allowance mailed Apr. 4, 2022", 7 pgs.
"U.S. Appl. No. 16/821,161, Response filed Jan. 27, 2022 to Non Final Office Action mailed Jan. 3, 2022", 8 pgs.
"U.S. Appl. No. 16/848,580, Examiner Interview Summary mailed Feb. 4, 2022", 3 pgs.
"U.S. Appl. No. 16/848,580, Examiner Interview Summary mailed Jun. 29, 2022", 2 pgs.
"U.S. Appl. No. 16/848,580, Final Office Action mailed May 10, 2022", 17 pgs.
"U.S. Appl. No. 16/848,580, Non Final Office Action mailed Jan. 4, 2022", 14 pgs.
"U.S. Appl. No. 16/848,580, Notice of Allowance mailed Aug. 31, 2022", 8 pgs.
"U.S. Appl. No. 16/848,580, Response filed Feb. 2, 2022 to Non Final Office Action mailed Jan. 4, 2022", 11 pgs.
"U.S. Appl. No. 16/848,580, Response filed Jun. 27, 2022 to Final Office Action mailed May 10, 2022", 12 pgs.
"U.S. Appl. No. 17/145,514, Examiner Interview Summary mailed Sep. 14, 2022", 2 pgs.
"U.S. Appl. No. 17/145,514, Non Final Office Action mailed Aug. 4, 2022", 7 pgs.
"U.S. Appl. No. 17/145,514, Notice of Allowance mailed Oct. 5, 2022", 5 pgs.
"U.S. Appl. No. 17/145,514, Response filed Sep. 26, 2022 to Non Final Office Action mailed Aug. 4, 2022", 8 pgs.
"Australian Application Serial No. 2017325823, First Examination Report mailed Jun. 19, 2019", 3 pgs.
"Australian Application Serial No. 2017334841, First Examination Report mailed Jun. 24, 2019", 3 pgs.
"Australian Application Serial No. 2017334841, Response filed Feb. 6, 2020 to First Examination Report mailed Jun. 24, 2019", 14 pgs.
"Australian Application Serial No. 2017335497, First Examination Report mailed Jun. 26, 2019", 13 pgs.
"Australian Application Serial No. 2017335497, Response filed Nov. 27, 2019 to First Examination Report mailed Jun. 26, 2019", 18 pgs.
"European Application Serial No. 17762308.9, Response to Communication pursuant to Rules 161 & 162 filed Nov. 26, 2019", 23 pgs.
"European Application Serial No. 17778108.5, Response to Communication Pursuant to Rules 161 and 162 filed Dec. 2, 2019", 3 pgs.
"European Application Serial No. 17794503.7, Response to Communication Pursuant to Rules 161 and 162 filed Dec. 30, 2019", 11 pgs.
"European Application Serial No. 18701908.8, Communication Pursuant to Article 94(3) EPC mailed May 20, 2020", 6 pgs.
"European Application Serial No. 18701908.8, Response filed Sep. 29, 2020 to Communication Pursuant to Article 94(3) EPC mailed May 20, 2020", 29 pgs.
"European Application Serial No. 18701908.8, Response to Communication Pursuant to Rules 161 and 162 filed Mar. 16, 2020", 8 pgs.
"European Application Serial No. 18702012.8, Response to Communication Pursuant to Rules 161 and 162 filed Mar. 11, 2020", 12 pgs.
"European Application Serial No. 18704105.8, Communication Pursuant to Article 94(3) EPC mailed Jan. 5, 2022", 9 pgs.
"European Application Serial No. 18704105.8, Response filed May 6, 2022 to Communication Pursuant to Article 94(3) EPC mailed Jan. 5, 2022", 35 pgs.
"European Application Serial No. 18704105.8, Response to Communication Pursuant to Rules 161 and 162 filed Feb. 27, 2020", 10 pgs.

(56) References Cited

OTHER PUBLICATIONS

"European Application Serial No. 21188652.8, Extended European Search Report mailed Nov. 24, 2021", 9 pgs.
"European Application Serial No. 21188652.8, Response filed Jul. 4, 2022 to Extended European Search Report mailed Nov. 24, 2021", 10 pgs.
"International Application Serial No. PCT/US2017/048867, International Preliminary Report on Patentability mailed Mar. 28, 2019", 8 pgs.
"International Application Serial No. PCT/US2017/048867, International Search Report mailed Nov. 13, 2017", 5 pgs.
"International Application Serial No. PCT/US2017/048867, Written Opinion mailed Nov. 13, 2017", 6 pgs.
"International Application Serial No. PCT/US2017/048896, International Preliminary Report on Patentability mailed Apr. 11, 2019", 8 pgs.
"International Application Serial No. PCT/US2017/048896, International Search Report mailed Nov. 27, 2017", 5 pgs.
"International Application Serial No. PCT/US2017/048896, Written Opinion mailed Nov. 27, 2017", 6 pgs.
"International Application Serial No. PCT/US2017/052685, International Preliminary Report on Patentability mailed Apr. 11, 2019", 6 pgs.
"International Application Serial No. PCT/US2017/052685, International Search Report mailed Jan. 4, 2018", 5 pgs.
"International Application Serial No. PCT/US2017/052685, Written Opinion mailed Jan. 4, 2018", 6 pgs.
"International Application Serial No. PCT/US2017/057367, International Preliminary Report on Patentability mailed May 9, 2019", 6 pgs.
"International Application Serial No. PCT/US2017/057367, International Search Report mailed Jan. 19, 2018", 4 pgs.
"International Application Serial No. PCT/US2017/057367, Written Opinion mailed Jan. 19, 2018", 4 pgs.
"International Application Serial No. PCT/US2018/013251, International Preliminary Report on Patentability mailed Jul. 25, 2019", 7 pgs.
"International Application Serial No. PCT/US2018/013251, International Search Report mailed Apr. 12, 2018", 4 pgs.
"International Application Serial No. PCT/US2018/013251, Written Opinion mailed Apr. 20, 2018", 5 pgs.
"International Application Serial No. PCT/US2018/013257, International Preliminary Report on Patentability mailed Jul. 25, 2019", 8 pgs.
"International Application Serial No. PCT/US2018/013257, International Search Report mailed Apr. 19, 2018", 4 pgs.
"International Application Serial No. PCT/US2018/013257, Written Opinion mailed Apr. 19, 2018", 6 pgs.
"International Application Serial No. PCT/US2018/013268, International Preliminary Report on Patentability mailed Jul. 25, 2019", 13 pgs.
"International Application Serial No. PCT/US2018/013268, International Search Report mailed Apr. 30, 2018", 5 pgs.
"International Application Serial No. PCT/US2018/013268, Written Opinion mailed Apr. 30, 2018", 11 pgs.
"International Application Serial No. PCT/US2018/041860, International Preliminary Report on Patentability mailed Jan. 30, 2020", 7 pgs.
"International Application Serial No. PCT/US2018/041860, International Search Report mailed Oct. 17, 2018", 4 pgs.
"International Application Serial No. PCT/US2018/041860, Written Opinion mailed Oct. 17, 2018", 5 pgs.
Ahern, David K., et al., "Comparison of lumbar paravertebral EMG patterns in chronic low back pain patients and non-patient controls", Pain, 34, (1988), 153-160.
Allum, John H.J., et al., "A speedy solution for balance and gait analysis: angular velocity measured at the centre of body mass", Current Opinion in Neurology 18, (2005), 15-21.
Alo, Kenneth M., et al., "Effect of Spinal Cord Stimulation on Sensory Nerve Conduction Threshold Functional Measures", Neuromodulation, vol. 3, No. 3, (2000), 145-154.
Ambady, Nalini, et al., "Thin Slices of Expressive Behavior as Predictors of Interpersonal Consequences: A Meta-Analysis", Psychological Bulletin, 1992, vol. 111, No. 2, 256-274.
Annoni, Elizabeth M., et al., "Method and Apparatus for Pain Management Using Objective Pain Measure", U.S. Appl. No. 62/400,336, filed Sep. 27, 2016.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Arsenault, Marianne, et al., "Pain Modulation Induced by Respiration: Phase and Frequency Effects", Neuroscience 252, (2013), 501-511.
Artner, Juraj, et al., "Prevalence of sleep deprivation in patients with chronic neck and back pain: a retrospective evaluation of 1016 patients", Journal of Pain Research: 6, (2013), 1-6.
Ashraf, A B, et al., "The painful face—Pain expression recognition using active appearance models", Image and Vision Computing Elsevier Guildford, GB, vol. 27, No. 12, (Nov. 1, 2009), 1788-1796.
Bakker, Jorn, et al., "What's your current stress level? Detection of stress patterns from GSR sensor data", Eindhoven University of Technology—The Netherlands, (2011), 1-8.
Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.
Banos, Oresti, et al., "PhysioDroid: Combining Wearable Health Sensors and Mobile Devices for a Ubiquitous, Continuous, and Personal Monitoring", The Scientific World Journal, vol. 2014 Article ID 190824, (2014), 11 pgs.
Bansevicius, Dalius, et al., "Mental stress of long duration: EMG activity, perceived tension, fatigue, and pain development in pain-free subjects", Headache: The Journal of Head and Face Pain; 37.8, (1997), 499-510.
Barad, Meredith J., et al., "Complex Regional Pain Syndrome Is Associated With Structural Abnormalities in Pain-Related Regions of the Human Brain", The Journal of Pain, vol. 15, No. 2, (Feb. 2014), 197-203.
Barkley, Jacob E., et al., "The effect of spinal cord stimulation unit revision on perceived pain, anxiety, mobility and physical activity in individuals with low back/lower extremity pain", Kent State University —The Spine and Pain Institute, Presented at Annual Meeting of the North American Neuromodulation Society (NANS) on Dec. 11-14, 2014, 1 pg.
Bartlett, Marian Stewart, et al., "Automatic Decoding of Facial Movements Reveals Deceptive Pain Expressions", Current Biology 24, 738-743, Mar. 31, 2014.
Beneck, George J., et al., "Spectral analysis of EMG using intramuscular electrodes reveals non-linear fatigability characteristics in persons with chronic low back pain", Journal of Electromyography and Kinesiology 23, (2013), 70-77.
Ben-Israel, Nir, et al., "Monitoring the nociception level: a multi-parameter approach", J Clin Monit Comput, (Jul. 2012), 10 pgs.
Ben-Israel, Nir, et al., "Monitoring the nociception level: a multi-parameter approach", J Clin Monit Comput 27, (2013), 659-668.
Berthomier, Christian, et al., "Automatic analysis of single-channel sleep EEG: validation in healthy individuals", Sleep-New York Then Westchester-30.11, (2007), 1587-1595.
Boselli, E., et al., "Prediction of immediate postoperative pain using the analgesia/nociception index: a prospective observational study", British Journal of Anaesthesia 112 (4):, (2014), 715-721.

(56) References Cited

OTHER PUBLICATIONS

Boselli, E., et al., "Prospective observational study of the non-invasive assessment of immediate postoperative pain using the analgesia/nociception index (ANI)", British Journal of Anaesthesia 111, (2013), 453-459.
Broucqsault-Dédrie, Celine, et al., "Measurement of Heart Rate Variability to Assess Pain in Sedated Critically Ill Patients: A Prospective Observational Study", PLOS One, (Jan. 25, 2016), 1-11.
Bunde, Armin, et al., "Correlated and uncorrelated regions in heart-rate fluctuations during sleep", Physical Review Letters 85.17, (2000), 3736-3739.
Chan, C. W.Y., et al., "Subjective pain sensation is linearly correlated with the Flexion reflex in man", Brain Research, 479, (1989), 145-150.
Chapman, C. Richard, et al., "Phasic pupil dilation response to noxious stimulation in normal volunteers: relationship to brain evoked potentials and pain report", (1999), 44-52.
Chen, Shuzhen, et al., "The role of the autonomic nervous system in hypertension: a bond graph model study", Physiological measurement 29.4 (2008): 473, (2008), 473-495.
Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013,, (2013), 1-10.
Chuang, Chiung-Cheng, et al., "Photoplethysmography variability as an alternative approach to obtain heart rate variability information in chronic pain patient", J Clin Monit Comput—Published online, (Feb. 24, 2015), 1-6.
Chung, OK Y., "Baroreflex sensitivity associated hypoalgesia in healthy states is altered by chronic pain", Pain 138, (2008), 87-97.
Ciampi De Andrade, Daniel, et al., "Neurophysiological assessment of spinal cord stimulation in failed back surgery syndrome", Pain 150, (2010), 485-491.
Cinaz, Burcu, et al., "Monitoring of mental workload levels during an everyday life office-work scenario", Pers Ubiquit Comput 17, (2013), 229-239.
Clark, Bryan Allen, et al., "Pain Management Based on Functional Measurements", U.S. Appl. No. 62/445,075, filed Jan. 11, 2017.
Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.
Dansie, Elizabeth J., et al., "Activity in Adults with Chronic Widespread Pain", The Journal of Pain—Accepted Manuscript, (2014), 33 pgs.
Davydov, Dmitry M., et al., "Cardiovascular activity and chronic pain severity", Physiology & Behavior 152, 203-216 (2015).
De-La-Herran, Alvaro M., et al., "Gait Analysis Methods: An Overview of Wearable and Non-Wearable Systems, Highlighting Clinical Applications", Sensors 14, (2014), 3362-3394.
Denk, Franziska, et al., "Chronic Pain: Emerging Evidence for the Involvement of Epigenetics". Neuron 73 (3), (2012), 435-444.
Duschek, S., "Relationship between baroreceptor cardiac reflex sensitivity and pain experience in normotensive individuals", International Journal of Psychophysiology 65, (2007), 193-200.
Eisenberg, Elon, et al., "Quantitative Sensory Testing for Spinal Cord Stimulation in Patients With Chronic Neuropathic Pain", (2006), 161-165.
Elgendi, Mohamed, "On the analysis of fingertip photoplethysmogram signals", Current cardiology reviews 8.1, (2012), 14-25.
Evans, Subhadr, et al., "Heart rate variability as a biomarker for autonomic nervous system response differences between children with chronic pain and healthy control children", Journal of Pain Research 3.6, (2013), 449-457.
Fagius, J., et al., "The cold pressor test: effects on sympathetic nerve activity in human muscle and skin nerve fascicles", Acta physiologica Scandinavica 137.3, (1989), 325-334.
Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.
Foo, H., et al., "Brainstem modulation of pain during sleep and waking", Sleep medicine reviews 7.2, (2003), 145-154.
Frederiks, Joost, et al., "Within-subject electrocardiogramences at equal heart rates: role of the autonomic nervous system", Pflügers Archiv 441.5, (2001), 717-724.
Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).
Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.
Gesche, Heiko, et al., "Continuous blood pressure measurement by using the pulse transit time: comparison to a cuff-based method", European journal of applied physiology 112.1, (2012), 309-315.
Godfrey, A., et al., "Direct measurement of human movement by accelerometry", Medical Engineering & Physics 30 (2008) 1364-1386.
Godfrey, A., et al., "Instrumenting gait with an accelerometer: a system and algorithm examination", Medical Engineering & Physics, Mar. 2015, doi:10.1016/j.medengphy.2015.02.003, 24 pgs.
Gouveia, S., et al., "Assessing Baroreflex Sensitivity in the Sequences Technique: Local versus Global Approach", Computers in Cardiology, 32, (2005), 279-282.
Granovsky, Yelena, et al., "Objective Correlate of Subjective Pain Perception by Contact Heat-Evoked Potentials", The Journal of Pain, vol. 9, No. 1, (Jan. 2008), 53-63.
Green, Alexande L., "Measurement of muscle sympathetic nerve activity reveals true sympathetic changes in chronic pain", Exp Physiol 97.10, (2012), 1083.
Hallman, David, et al., "Autonomic regulation, physical activity and perceived stress in subjects with musculoskeletal pain: 24-hour ambulatory monitoring", International Journal of Psychophysiology 86, (2012), 276-282.
Hallman, David M., et al., "Changes in physical activity and heart rate variability in chronic neck-shoulder pain: monitoring during work and leisure time", Int Arch Occup Environ Health 87, (2014), 735-744.
Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907482, 11 pages, http://dx.doi.org/10.1155/2015/907482, 11 pages.
Hartwich, Doreen, et al., "Effect of muscle metaboreflex activation on spontaneous cardiac baroreflex sensitivity during exercise in humans", J Physiol 589.24, (2011), 6157-6171.
Jensen, MP, et al., "Brain EEG activity correlates of chronic pain in persons with spinal cord injury: clinical implications", Nature; Spinal Cord; 51, (Jul. 17, 2012), 55-58.
Jess, Gunnar, et al., "Monitoring heart rate variability to assess experimentally induced pain using the analgesia nociception index—A randomised volunteer study", Eur J Anaesthesiol 32, (2015), 1-8.
Kang, Jon-Eun, et al., "Pulse transit time shows vascular changes caused by propofol in children", J Clin Monit Comput 29, (2015), 533-537.
Keefe, Francis J., et al., "An Objective Approach to Quantifing Pain Behavior and Gait Patterns in Low Back Pain Patients", Pain, 21, (1985), 153-161.
Kemler, Marius A., et al., "Impact of Spinal Cord Stimulation on Sensory Characteristics in Complex Regional Pain Syndrome Type 1—A Randomized Trial", Anesthesiology, 95, (2001), 72-80.
Keshari, Kayvan R., et al., "Lactic Acid and Proteoglycans as Metabolic Markers dor Discogenic Back Pain", SPINE, vol. 13, No. 3, (2008), 312-317.
Kim, Young Uk, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.

(56) References Cited

OTHER PUBLICATIONS

Kodituwakku, Sandun, et al., "Point Process Respiratory Sinus Arrhythmia Analysis during Deep Tissue Pain Stimulation", Computing in Cardiology 38, (2011), 193-196.
Koenig, J., et al., "Heart rate variability and experimentally induced pain in healthy adults: A systematic review", European Journal of Pain 18, (2014), 301-314.
Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.
La Rovere, Maria Teresa, et al., "Baroreflex Sensitivity: Measurement and Clinical Implications", Ann Noninvasive Electrodardiol, 13(2):191-207, 2008.
Lamoth, Claudine J.C., et al., "How do persons with chronic low back pain speed up and slow down? Trunk-pelvis coordination and erector spinae activity during gait", Gait & Posture 23, (2006), 230-239.
Lamoth, Claudine J.C., et al., "Pelvis-Thorax Coordination in the Transverse Plane During Walking in Persons With Nonspecific Low Back Pain", SPINE, vol. 27, No. 4, (2002), E92-E99.
Lane, James D., et al., "Respiratory Sinus Arrhythmia and Cardiovascular Responses to Stress", Psychophysiology, vol. 29, No. 4, (1992), 461-470.
Latremoliere, Alban, et al., "Reduction of Neuropathic and Inflammatory Pain through Inhibition of the Tetrahydrobiopterin Pathway", Neuron, 86 (6), (2015), 1393-1406.
Ledowski, Thomas, et al., "The influence of age and sex on the relationship between heart rate variability, haemodynamic variables and subjective measures of acute post-operative pain", European Journal of Anesthesiology, vol. 28, No. 6, (2011), 433-437.
Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.
Lidberg, Lars, et al., "Sympathetic Skin Nerve Dischai gcs in Relation lo Anipliliule ol Skin Resistance Responses", Psychophysiology, vol. 18, No. 3, (May 1981), 268-270.
Littlewort, Gwen C., et al., "Automatic Coding of Facial Expressions Displayed During Posed and Genuine Pain", Image and Vision Computing, 27(12) p. 1741-1844.
Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Looney, David, et al., "The In-the-Ear Recording Concept", IEEE Pulse Nov./Dec. 2012, 32-42.
Marchi, Antonio, et al., "Pain Biomarkers", Clin Drug Invest, 29 Suppl 1, (2009), 41-46.
Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C,, et al., "Quantitative sensory testing in the German Research Network on Neuropathic Pain (DFNS): Somatosensory abnormalities in 1236 patients with different neuropathic pain syndromes", Pain 150, (2010), 439-450.
Mcbeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.
Mccarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.
Mccracken, Lance M., et al., "Disrupted sleep patterns and daily functioning in patients with chronic pain", Pain Res Manage vol. 7 No. 2 Summer 2002 75-79.

Mikkelsen, Kaare B., et al., "EEGRecordedfromthe-Ear:CharacterizingtheEar-EEGMethod", FrontiersinNeuroscience |www.frontiersin.org, Nov. 2015|vol. 9|Article438, 8 pgs.
Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.
Moseley, G. Lorimer, et al., "Tactile Discrimination, but not tactile stimulation alone, reduces chronic limg pain", Pain 137, (2008), 600-608.
Moxham, I.M., "Understanding Arterial Pressure Waveforms", Southern African Journal of Anaesthesia and Analgesia 9.1, (2003), 40-42.
Mukkamala, R., et al., "Toward ubiquitous blood pressure monitoring via pulse transit time: theory and practice", IEEE Transactions on Biomedical Engineering 62.8, (2015), 1879-1901.
Mylius, Vett, et al., "Sex differences in nociceptive withdrawal reflex and pain perception", Somatosensory and Motor Research 22 (3), (Sep. 2005), 207-211.
Neblett, Randy, et al., "What Is The Best Surface EMG Measure of Lumbar Flexion-Relation for Distinguishing Chronic Low Back Pain Patients From Pain-Free Controls?", Clin J Pain 29 (4)—NIH Public Access, (Apr. 2013), 334-340.
Ng, Joseph, et al., "EMG activity of trunk muscles and torque output during isometric axial rotation exertion: a comparison between back pain patients and matched controls", Journal of Orthopaedic Research; 20, (2002), 112-121.
Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.
Panjabi, Manohar, "Clinical spinal instability and low back pain", Journal of Electromyography and Kinesiology 13, (2003), 371-379.
Patti, Gary J., et al., "Metabolomics implicates altered sphingolipids in chronic pain of neuropathic origin", nature chemical biology, vol. 8, (Mar. 2012), 232-234.
Perruchoud, Christophe, et al., "Assessment of Physical Activity of Patients with Chronic Pain", Neuromodulation: Technology at the Neural Interface; 17, (2012), 42-47.
Pinheiro, Eulália Silva Dos Santos, et al., "Electroencephalographic Patterns in Chronic Pain: A Systematic Review of the Literature", PLOS ONE | DOI:10.1371/journal.pone.0149085 Feb. 25, 2016, 27 pgs.
Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.
Pleger, Burkhard, et al., "Patterns of cortical reorginization parallel impaired tactile discrimination and pain intensity in complex regional pain syndrome", NeuroImage 32, (2006), 503-510.
Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.
Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.
Prichep, Leslie S., et al., "Evaluation of the Pain Matrix Using EEG Source Localization: A Feasibility Study", Pain Medicine 12, (2011), 1241-1248.
Prkachin, Kenneth, "The consistency of facial expressions of pain: a comparison across modalities", PAIN, 51, (1992), 279-306.
Raminen, Tina, et al., "The Impact of Spinal Cord Stimulation on Sleep Patterns", Neuromodulation 19, (2016), 477-481.
Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.
Rhudy, Jamie L., et al., "Defining the nociceptive flexion reflex (NFR) threshold in human participants: A comparison of different scoring criteria", Pain 128, (2007), 244-253.

(56) References Cited

OTHER PUBLICATIONS

Roy, Sourav Dey, et al., "An Approach for Automatic Pain Detection through Facial Expression", Procedia Computer Science 84 (2016) 99-106.
Sacco, Marcella, et al., "The Relationship Between Blood Pressure and Pain", The Journal of Clinical Hypertension vol. 15, No. 8, (Aug. 2013), 600-605.
Sano, Akane, et al., "Quantitative analysis of wrist electrodermal activity during sleep", Int J Psychophysiol. Dec. 2014 ; 94(3), (2014), 382-389.
Sarnthein, Johannes, et al., "Increased EEG power and slowed dominant frequncy in patients with neurogenic pain", Brain 129, (2005), 55-64.
Sato, Karina L/, et al., "Spinal Cord Stimulation (SCS) Improves Decreased Physical Activity Induced by Nerve Injury", Behavioral Neuroscience, vol. 128, No. 5, (2914), 625-632.
Sawada, Yukihiro, et al., "Normalized pulse volume (NPV) derived photo-plethysmography as a more valid measure of the finger vascular tone", International Journal of Psychophysiology 41, (2001), 1-10.
Sayar, Kemal, et al., "Sleep Quality in Chronic Pain Patients", Can J. Psychiatry, vol. 47, No. 9, (Nov. 2002), 844-848.
Schulman, Joshua J., et al., "Thalamocortical dysrhythmia syndrome: MEG imaging of neuropathic pain", (Jul. 25, 2014), 33-39.
Schulz, Enrico, et al., "Prefrontal Gamma Oscillations Encode Tonic Pain in Humans", Cerebral Cortex 2015, (Mar. 8, 2015), 1-8.
Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.
Shouldice, R., "PR and PP ECG intervals as indicators of autonomic nervous innervation of the cardiac sinoatial and atrioventricular nodes", Neural Engineering, 2003. Conference Proceedings. First International IEEE Embs Conference on. IEEE, (Mar. 2003), 261-264.
Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.
Sihvonen, T., et al., "Electric behavior of low back muscles during lumbar pelvic rhythm in low back pain patients and healthy controls", Archives of physical medicine and rehabilitation; 72.13, (1991), 1080-1087.
Simoes, Mario A., "Feasibility of Wearable Sensors to Determine Gait Parameters", University of South Florida Scholar Commons, (2011), 1-98.
Skljarevski, V., et al., "The nociceptive flexion reflex in humans—review article", Pain, 96, (2002), 3-8.
Smallwood, Rachel F., et al., "Structural Brain Anomalies and Chronic Pain: A Quantitative Meta-Analysis of Gray Matter Volume", The Journal of Pain, vol. 14, No. 7, (Jul. 2013), 663-675.
Sotocinal, S G, et al., "The Rat Grimace Scale partially automated method for quantifying pain in the laboratory rat via facial expressions", Molecular Pain Biomed Central, London, GB, vol. 7 No. 1, (Jul. 29, 2011), 1744-8069.
Srivastava, Kyle Harish, et al., "Pain Management Based on Cardiovascular Parameters", U.S. Appl. No. 62/445,053, filed Jan. 11, 2017.
Srivastava, Kyle Harish, et al., "Pain Management Based on Emotional Expression Measurements", U.S. Appl. No. 62/445,082, filed Jan. 11, 2017.
Staud, Roland, "Heart rate variability as a biomarker of fibromyalgia syndrome", Fut Rheumatol 3 (5)—NIH Public Access, (Oct. 1, 2008), 475-483.
Storm, H., et al., "Skin conductance correlates with perioperative stress", Acta Anaesthesiol Scand 46, (2002), 887-895.
Sturgeon, John A., et al., "Respiratory Sinus Arrhythmia: a Marker of Resilience to Pain Induction", Int.J. Behav. Med. 21, (2014), 961-965.
Swenne, C. A., "Baroreflex sensitivity: mechanisms and measurement", Neth Heart J 21, (2013), 58-60.
Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.
Tagliazucchi, Enzo, et al., "Brain resting state is disrupted in chronic back pain patients", Neurosci Lett. 485 (1)—NIH Public Access, (Nov. 12, 2010), 26-31.
Tao, Weijun, et al., "Gait Analysis Using Wearable Sensors", Sensors 12, (2012), 2255- 2283.
Tauda, Makoto, et al., "P2X4receptorsandneuropathicpain", Frontiers in Cellular Neuroscience, vol. 7, Article 191, (Oct. 28, 2013), 1-6.
Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.
Thakur, Pramodsingh Hirasingh, et al., "Method and Apparatus for Pain Control Using Baroreflex Sensitivity During Posture Change", U.S. Appl. No. 62/412,587, filed Oct. 25, 2016.
Thakur, Pramodsingh Hirasingh, et al., "Systems and Methods for Closed-Loop Pain Management", U.S. Appl. No. 62/400,313, filed Sep. 27, 2016.
Thankur, Pramodsingh Hirasingh, et al., "Method and Apparatus for Pain Management Using Heart Sounds", U.S. Appl. No. 62/395,641, filed Sep. 16, 2016.
Theuvenel, Peter J., et al., "Responses to Median and Tbial Nerve Stimulation in Patients with Chronic Neuropathic Pain", Brain Topography, vol. 11, No. 4, (1999), 306-313.
Uceyler, Nuncan, et al., "Differential expression of cytokines in painful and painless neuropathies", (2007).
Uzar, E., et al., "Serum cytokine and pro-brain natriuretic peptide (BNP) levels in patients with migraine", European Review for Medical and Pharmacological Sciences; 15, (2011), 1111-1116.
Van Velzen, Marit H.N., et al., "Effect of heat-induced pain stimuli on pulse transit time and pulse wave amplitude in healthy volunteers", Physiological Measurement 37, (2016), 52-66.
Villarejo, Viqueira Maria, et al., "A Stress Sensor Based on Galvanic Skin Response (GSR) Controlled by ZigBee", Sensors 12, (2012), 6075-6101.
Walton, K. D., et al., "Abnormal thalamocortical activity in patients with Complex Regional Pain Syndrome (CRPS) Type 1", Pain 150, (2010), 41-51.
Willer, Jean Claude, "Comparative Study of Perceived Pain and Nociceptive Flexion Reflex in Man", Pain, 3, (1977), 69-80.
Williams, Dewayne P., et al., "Effects of Chronic Pelvic Pain on Heart Rate Variability in Women", The Journal of Urology, vol. 194,, (Nov. 2015), 1-6.
Wong, Arnold Y.L., et al., "Does experimental low back pain change posteroanterior lumbar spinal stiffness and trunk muscle activity? A randomized crossover study", Clinical Biomechanics 34, (2016), 45-52.
Wong, Jih-Sen, et al., "A comparative study of pulse rate variability and heart rate variability in healthy subjects", J Clin Monit Comput 26, (2012), 107-114.
Wu, Hao-Yu, et al., "Eulerian Video Magnification for Revealing Subtle Changes in the World", ACM Transactions on Graphics 31(4), (2012), 1-8.
Zamuner, Antonio R., et al., "Respiratory Sinus Arrhythmia and its Association with Pain in Women with Fibromyalgia Syndrome", Pain Practice, vol. 16, Issue 6, (2016), 704-711.
Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.
Zeng, Zhihong, et al., "A Survey of Affect Recognition Methods: Audio, Visual and Spontaneous Expressions", ICMI'07, Nov. 12-15, 2007, 126-133.
Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.

(56) References Cited

OTHER PUBLICATIONS

Zhou, Jing, et al., "Recurrent Convolutional Neural Network Regression for Continuous Pain Intensity Estimation in Video", arXiv preprint arXiv:1605.00894 (2016) 84-92.

Zhou, Jing, et al., "Recurrent Convolutional Neural Network Regression for Continuous Pain Intensity Estimation in Video", Technical Report, (May 3, 2016), 1-11.

"U.S. Appl. No. 16/986,519, Non Final Office Action mailed Oct. 5, 2022", 11 pgs.

"U.S. Appl. No. 16/986,519, Notice of Allowance mailed Apr. 24, 2023", 8 pgs.

"U.S. Appl. No. 16/986,519, Response filed Jan. 4, 2023 to Non Final Office Action mailed Oct. 5, 2022", 10 pgs.

"U.S. Appl. No. 17/095,642, Non Final Office Action mailed Feb. 17, 2022", 13 pgs.

"U.S. Appl. No. 17/095,642, Notice of Allowance mailed May 4, 2022", 8 pgs.

"U.S. Appl. No. 17/095,642, Response filed Mar. 31, 2022 to Non Final Office Action mailed Feb. 17, 2022", 9 pgs.

"U.S. Appl. No. 17/145,514, Examiner Interview Summary mailed Jan. 18, 2023", 2 pgs.

"U.S. Appl. No. 17/188,300, Examiner Interview Summary mailed Dec. 14, 2022", 2 pgs.

"U.S. Appl. No. 17/188,300, Non Final Office Action mailed Sep. 22, 2022", 15 pgs.

"U.S. Appl. No. 17/385,665, Advisory Action mailed May 17, 2024", 4 pgs.

"U.S. Appl. No. 17/385,665, Examiner Interview Summary mailed May 14, 2024", 2 pgs.

"U.S. Appl. No. 17/385,665, Examiner Interview Summary mailed Dec. 11, 2023", 2 pgs.

"U.S. Appl. No. 17/385,665, Final Office Action mailed Mar. 22, 2024", 13 pgs.

"U.S. Appl. No. 17/385,665, Non Final Office Action mailed Jul. 5, 2024", 9 pgs.

"U.S. Appl. No. 17/385,665, Non Final Office Action mailed Sep. 14, 2023", 11 pgs.

"U.S. Appl. No. 17/385,665, Response filed May 10, 2024 to Final Office Action mailed Mar. 22, 2024", 11 pgs.

"U.S. Appl. No. 17/385,665, Response filed Dec. 14, 2023 to Non Final Office Action mailed Sep. 14, 2023", 10 pgs.

"U.S. Appl. No. 17/848,149, Non Final Office Action mailed Aug. 11, 202023", 10 pgs.

"U.S. Appl. No. 17/848,149, Notice of Allowance mailed Sep. 15, 2023", 7 pgs.

"U.S. Appl. No. 17/848, 149, Response filed Sep. 5, 2023 to Non Final Office Action mailed Aug. 11, 2023", 8 pgs.

"U.S. Appl. No. 18/077,981, Non Final Office Action mailed May 25, 2023", 7 pgs.

"U.S. Appl. No. 18/077,981, Notice of Allowance mailed Jul. 7, 2023", 7 pgs.

"U.S. Appl. No. 18/077,981, Response filed Jun. 8, 2023 to Non Final Office Action mailed May 25, 2023", 7 pgs.

"European Application Serial No. 17794503.7, Communication Pursuant to Article 94(3) EPC mailed Nov. 7, 2022", 3 pgs.

"European Application Serial No. 17794503.7, Response filed Feb. 15, 2023 to Communication Pursuant to Article 94(3) EPC mailed Nov. 7, 2022", 21 pgs.

"European Application Serial No. 18702012.8, Communication Pursuant to Article 94(3) EPC mailed Jan. 25, 2023", 5 pgs.

"European Application Serial No. 21188652.8, Communication Pursuant to Article 94(3) EPC mailed May 2, 2024", 5 pgs.

"European Application Serial No. 21188652.8, Response filed Jul. 24, 2024 to Communication Pursuant to Article 94(3) EPC mailed May 2, 2024", 7 pgs.

\* cited by examiner

PAIN MANAGEMENT BASED ON EMOTIONAL EXPRESSION MEASUREMENTS

CLAIM OF PRIORITY

This application is a continuation of U.S. application Ser. No. 17/145,514, filed Jan. 11, 2021, which is a continuation of U.S. application Ser. No. 15/867,873, filed Jan. 11, 2018, which claims the benefit of priority under 35 U.S.C. § 119(e) of U.S. Provisional Patent Application Ser. No. 62/445,082, filed on Jan. 11, 2017, each of which is herein incorporated by reference in its entirety.

CROSS REFERENCE TO RELATED APPLICATIONS

This application is related to commonly assigned U.S. Provisional Patent Application Ser. No. 62/445,053, entitled "PAIN MANAGEMENT USING CARDIOVASCULAR PARAMETERS", filed on Jan. 11, 201, U.S. Provisional Patent Application Ser. No. 62/445,061, entitled "PAIN MANAGEMENT BASED ON BRAIN ACTIVITY MONITORING", filed on Jan. 11, 2017, U.S. Provisional Patent Application Ser. No. 62/445,069, entitled "PAIN MANAGEMENT BASED ON RESPIRATION-MEDIATED HEART RAPES", filed on Jan. 11, 2017, U.S. Provisional Patent Application Ser. No. 62/445,075, entitled "PAIN MANAGEMENT BASED ON FUNCTIONAL MEASUREMENTS", filed on Jan. 11, 2017, U.S. Provisional Patent Application Ser. No. 62/445,092, entitled "PAIN MANAGEMENT BASED ON MUSCLE TENSION MEASUREMENTS", filed on Jan. 11, 2017, U.S. Provisional Patent Application Ser. No. 62/445,095, entitled "PATIENT-SPECIFIC CALIBRATION OF PAIN QUANTIFICATION", filed on Jan. 11, 2017, U.S. Provisional Patent Application Ser. No. 62/395,641, entitled "METHOD AND APPARATUS FOR PAIN MANAGEMENT USING HEART SOUNDS", filed on Sep. 16, 2016, U.S. Provisional Patent Application Ser. No. 62/400,313, entitled "SYSTEMS AND METHODS FOR CLOSED-LOOP PAIN MANAGEMENT", filed on Sep. 27, 2016, U.S. Provisional Patent Application Ser. No. 62/400,336, entitled "METHOD AND APPARATUS FOR PAIN MANAGEMENT USING OBJECTIVE PAIN MEASURE", filed on Sep. 27, 2016, U.S. Provisional Patent Application Ser. No. 62/412,587, entitled "METHOD AND APPARATUS FOR PAIN CONTROL USING BAROREFLEX SENSITIVITY DURING POSTURE CHANGE", filed on Oct. 25, 2016, which are incorporated by reference in their entirety.

TECHNICAL FIELD

This document relates generally to medical systems and more particularly to systems, devices, and methods for pain management.

BACKGROUND

Pain is one of the most common and among the most personally compelling reasons for seeking medical attention, and consumes considerable healthcare resources each year. The relation between etiology, underlying mechanisms and the specific symptoms and signs related to painful disorders is complex. Pain in an individual patient may be produced by more than one mechanism.

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain. Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system).

Chronic pain may be treated or alleviated using medications, acupuncture, surgery, and neuromodulation therapy such as local electrical stimulation or brain stimulation, among others. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), which can electrically stimulate tissue or nerve centers to treat nervous or muscular disorders. In an example, an IPG can deliver electrical pulses to a specific region in a patient's spinal cord, such as particular spinal nerve roots or nerve bundles, to create an analgesic effect that masks pain sensation.

SUMMARY

By way of example, chronic pain management may involve determining appropriate treatment regimens such as SCS and evaluating therapy efficacy. Accurate pain assessment and characterization are desirable for managing patients with chronic pain. Currently, pain assessment generally relies on patient subjective report of pain symptoms, including severity, pattern, or duration of pain. Based on the patient reported pain sensation, a clinician may prescribe a pain therapy, such as to manually program an electrostimulator for delivering a neuromodulation therapy. However, the subjective description of pain sensation may be constrained by patient cognitive abilities. The subjective pain description may also be subject to intra-patient variation, such as due to a progression of a chronic disease, or a change in general health status or medication. Having a patient to report and describe each pain episode he or she has experienced is not efficient and may delay appropriate pain therapy. Additionally, for patients in an ambulatory setting who lack immediate access to medical assistance, manual adjustment of pain therapy by a clinician may not be feasible especially if immediate therapy titration is required. The present inventors have recognized that there remains a demand for improving pain management, such as systems and methods for objective pain assessment and automated closed-loop pain therapy based on objective pain assessment.

This document discusses, among other things, systems, devices, and methods for assessing pain in a subject. The system includes sensors to sense information corresponding to the subject's emotional reaction to pain. The system may extract one or more signal metrics of facial or vocal expression from the sensed information corresponding to the emotional reaction to pain, and generate a pain score using the one or more signature metrics. The pain score can be output to a system user, or used for closed-loop control of a pain therapy.

Example 1 is a system for managing pain of a patient. The system comprises a sensor circuit, a pain analyzer circuit, and an output unit. The sensor circuit may be coupled to one or more sensors and configured to sense from the patient information corresponding to patient emotional reaction to pain; a pain analyzer circuit coupled to the sensor circuit. The pain analyzer circuit may be configured to generate, from the sensed information corresponding to the patient emotional reaction to pain, one or more signal metrics of facial or vocal expression, and generate a pain score using the generated one or more signal metrics. The output unit configured to output the pain score to a user or a process.

In Example 2, the subject matter of Example 1 optionally includes an electrostimulator configured to generate electrostimulation energy to treat pain, and a controller circuit coupled to the pain analyzer circuit and the electrostimulator. The controller circuit may be configured to control the electrostimulator to deliver a pain therapy and to control the electrostimulation energy generated by the electrostimulator according to the pain score.

In Example 3, the subject matter of Example 2 optionally includes the electrostimulator that may be further configured to deliver at least one of: a spinal cord stimulation; a brain stimulation; or a peripheral nerve stimulation.

In Example 4, the subject matter of any one or more of Examples 2-3 optionally includes the controller circuit that may be configured to deliver first electrostimulation to the patient in response to the pain score exceeding a threshold value, and to deliver second electrostimulation to the patient in response to the pain score falling below the threshold value. The first electrostimulation may differ from the second electrostimulation with respect to at least one of an electrostimulation energy, an electrostimulation pulse shape, or an electrostimulation pattern.

In Example 5, the subject matter of any one or more of Examples 1-4 optionally includes the sensor circuit that may be coupled to a camera configured to capture a facial image of the patient. The pain analyzer circuit may be further configured to produce, from the facial image, a plurality of image features of a facial landmark, and to generate the pain score using the image features.

In Example 6, the subject matter of Example 5 optionally includes the pain analyzer circuit that may be further configured to generate the pain score based on a comparison of the produced plurality of image features and a facial image template.

In Example 7, the subject matter of any one or more of Examples 1-6 optionally includes the sensor circuit that may be coupled to a voice recorder configured to record a speech signal of the patient. The pain analyzer circuit may be configured to generate from the recorded speech signal a plurality of speech features, and to generate the pain score using the plurality of speech features.

In Example 8, the subject matter of Example 7 optionally includes the plurality of speech features correspond to speech motor control.

In Example 9, the subject matter of any one or more of Examples 1-8 optionally includes the sensor circuit coupled to an accelerometer sensor configured to sense skull vibration signal during patient speech. The pain analyzer circuit may be configured to generate, from the sensed skull vibration signal during patient speech, a plurality of vibration features, and to generate the pain score using the generated plurality of vibration features.

In Example 10, the subject matter of any one or more of Examples 1-9 optionally includes the one or more sensors configured to sense the information corresponding to the patient emotional reaction to pain are incorporated in a mobile device communicatively coupled to the pain analyzer circuit.

In Example 11, the subject matter of Example 10 optionally includes the mobile device that may be configured for wireless communication and to execute an application to detect the facial or vocal expression.

In Example 12, the subject matter of any one or more of Examples 1-11 optionally include the pain analyzer circuit that may be further configured to generate the pain score using a combination of a plurality of the signal metrics each weighted by their respective weight factor.

In Example 13, the subject matter of any one or more of Examples 1-12 optionally includes the pain analyzer circuit that may be further configured to generate the pain score using a combination of comparisons between the plurality of the signal metrics and respective threshold values.

In Example 14, the subject matter of any one or more of Examples 1-13 optionally includes the output unit that may be further configured to produce an alert based on the pain score.

In Example 15, the subject matter of any one or more of Examples 2-14 optionally includes an implantable neuromodulator device (IND) that includes one or more of the sensor circuit, the pain analyzer circuit, or the electrostimulator.

Example 16 is a method for managing pain of a patient using an implantable neuromodulator device (IND). The method comprises: sensing, from the patient via a sensor circuit, information corresponding to patient emotional reaction to pain; generating, from the sensed information corresponding to the patient emotional reaction to pain, one or more signal metrics of facial or vocal expression; generating a pain score based on the one or more signal metrics; and outputting the pain score to a user or a process.

In Example 17, the subject matter of Example 16 optionally includes delivering a pain therapy via the IND. The pain therapy may include electrostimulation energy determined according to the pain score.

In Example 18, the subject matter of any one or more of Examples 16-17 optionally includes the information corresponding to patient emotional reaction to pain includes a facial image of the patient. The one or more signal metrics may include a plurality of image features of a facial landmark generated from the sensed facial image.

In Example 19, the subject matter of Example 18 optionally includes generating the pain score including using a comparison of the produced plurality of image features and a facial image template.

In Example 20, the subject matter of any one or more of Examples 16-19 optionally includes the information corresponding to the patient emotional reaction to pain that may include a speech signal of the patient. The one or more signal metrics may include a plurality of speech features generated from the sensed speech signal.

In Example 21, the subject matter of Example 20 optionally includes a plurality of speech features corresponding to speech motor control.

In Example 22, the subject matter of any one or more of Examples 16-21 optionally includes the information corresponding to the patient emotional reaction to pain that may include skull vibration signal during patient speech. The one or more signal metrics include a plurality of vibration features generated from the sensed skull vibration signal during patient speech.

In Example 23, the subject matter of any one or more of Examples 16-22 optionally includes generating the pain score using a combination of a plurality of the signal metrics each weighted by their respective weight factor.

The pain score generated based on sensor signals indicative of patient emotional reactions to pain, such as based on the facial or vocal expressions as discussed in this document, may improve medical diagnostics of automated characterization of patient pain, as well as individualized therapies to alleviate pain and to reduce side effects. The systems, devices, and methods discussed in this document may also enhance the performance and functionality of a pain management system or device. A device or a system programmed with the sensor-based pain assessment methods can have improved automaticity in medical diagnostics. More efficient device memory or communication bandwidth usage may be achieved by storing or transmitting medical information more relevant to clinical decisions. Additionally, through improved pain therapy based on patient individual need and therapy efficacy, battery longevity of an implantable device may be enhanced, or pain medication volume may be saved.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
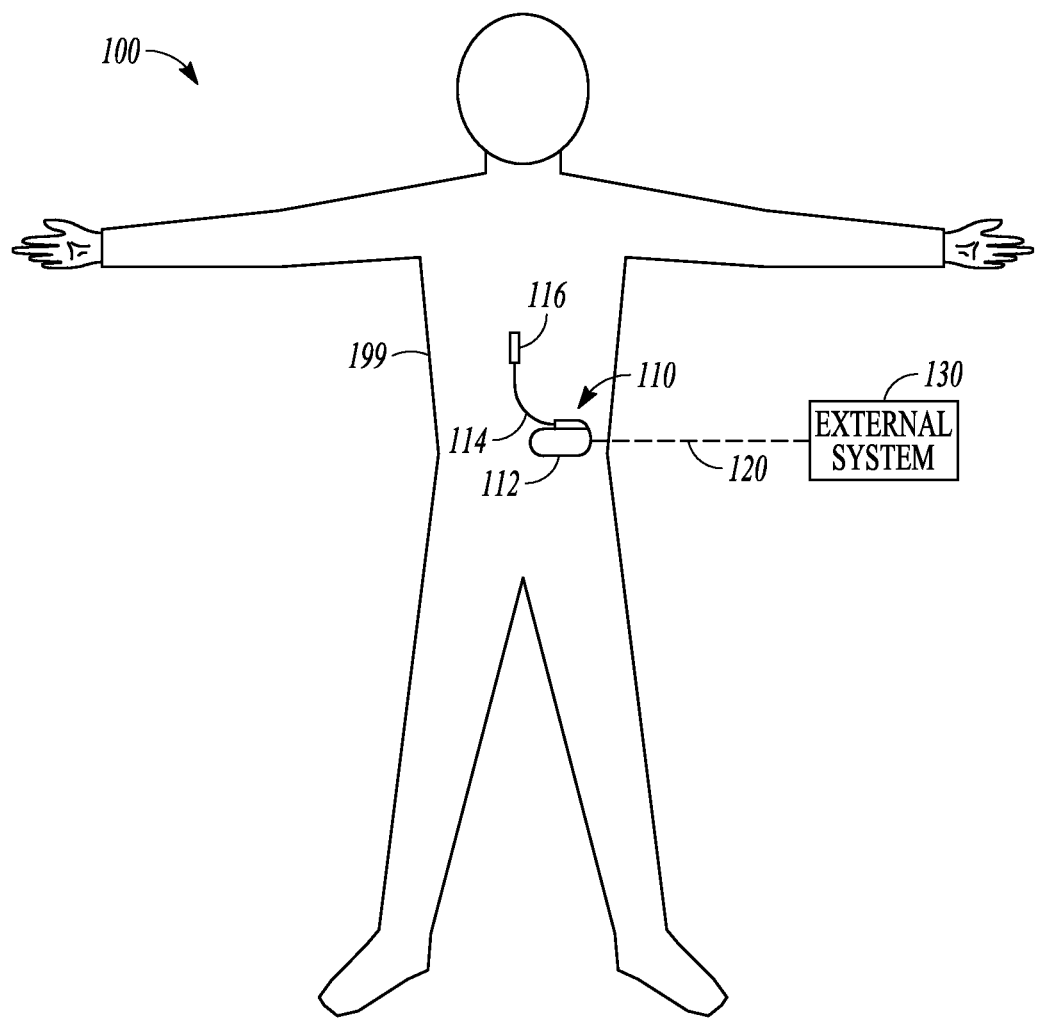
FIG. 1 illustrates, by way of example and not limitation, a neuromodulation system and portions of an environment in which the neuromodulation system may operate.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Clinically, chronic pain may affect a patient's cognitive function, and cause emotional and psychological distress, depression, and motor control impairment. Normal speech production requires integration and integrity of cognitive, neuromuscular, and musculoskeletal activities. The underlying complexity of speech motor activities renders speech production vulnerable to subtle abnormalities in neurological or psychomotor functioning. In some patients, chronic pain may directly or indirectly result in abnormality in speech motor control, causing changes in vocal or behavioral expressions. Some patients may also present with characteristic facial expressions when a pain episode occurs or when pain worsens. Therefore, close monitoring and detection of changes in patient emotional expressions may provide an objective assessment of pain, and may be used to improve pain therapy efficacy.

Disclosed herein are systems, devices, and methods for or assessing pain in a subject, and optionally programming pain therapy based on the pain assessment. In various embodiments, the present system may include sensors configured to sense from the subject information corresponding to patient emotional reaction to pain. A pain analyzer circuit may generate a pain score using signal metrics of facial, vocal, or behavioral expression that are extracted from the sensed information corresponding to the patient emotional reaction to pain. The system may include a neurostimulator that can adaptively control the delivery of pain therapy by automatically adjusting stimulation parameters based on the pain score.

The present system may be implemented using a combination of hardware and software designed to provide a closed-loop pain management regimen to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, and Vagus Nerve Stimulation (VNS) therapies. In various examples, instead of providing closed-loop pain therapies, the systems, devices, and methods described herein may be used to monitor the patient and assess pain that either occurs intrinsically or is induced by nerve block procedures or radiofrequency ablation therapies, among others. The patient monitoring may include generating recommendations to the patient or a clinician regarding pain treatment.

FIG. 1 illustrates, by way of example and not limitation, an example of a neuromodulation system 100 for managing pain in a subject such as a patient with chronic pain, and portions of an environment in which the neuromodulation system 100 may operate. The neuromodulation system 100 may include an implantable system 110 that may be associated with a body 199 of the subject, and an external system 130 in communication with the implantable system 110 via a communication link 120.

The implantable system 110 may include an ambulatory medical device (AMD), such as an implantable neuromodulator device (IND) 112, a lead system 114, and one or more electrodes 116. The IND 112 may be configured for subcutaneous implant in a patient's chest, abdomen, or other parts of the body 199. The IND 112 may be configured as a monitoring and diagnostic device. The IND 112 may include a hermetically sealed can that houses sensing circuitry to sense physiological or functional signals from the patient via sensing electrodes or ambulatory sensors associated with the patient and in communication with the IND 112. In some examples, the sensing electrodes or the ambulatory sensors may be included within the IND 112. The physiological or functional signals may be measured during a pain episode. In an example, the sensor signals may contain information corresponding to patient emotional reaction to pain. The emotional reaction may be presented by patient's facial, vocal, or behavioral expression, among other emotional expressions. The various emotional expressions may be correlative to severity of the pain. The IND 112 may characterize and quantify the pain, such as to determine onset, intensity, severity, duration, or patterns of the pain experienced by the subject. The IND 112 may generate an alert to indicate occurrence of a pain episode, pain exacerbation, or efficacy of pain therapy, and present the alert to a clinician.

The IND 112 may alternatively be configured as a therapeutic device for treating or alleviating the pain. In addition to pain monitoring circuitry, the IND 112 may further include a therapy unit that can generate and deliver energy or modulation agents to a target tissue. The energy may include electrical, magnetic, or other types of energy. In some examples, the IND 112 may include a drug delivery system such as a drug infusion pump that can deliver pain medication to the patient, such as morphine sulfate or ziconotide, among others.

The IND 112 may include electrostimulation circuitry that generates electrostimulation pulses to stimulate a neural target via the electrodes 116 operably connected to the IND 112. In an example, the electrodes 116 may be positioned on or near a spinal cord, and the electrostimulation circuitry may be configured to deliver SCS to treat pain. In another example, the electrodes 116 may be surgically placed at other neural targets such as a brain or a peripheral neutral tissue, and the electrostimulation circuitry may be configured to deliver brain or peripheral stimulations. Examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic nerve modulation, adrenal gland modulation, baroreceptor stimulation, or transcranial magnetic stimulation, spinal cord stimulation (SCS), dorsal root ganglia (DRG) stimulation, motor cortex stimulation (MCS), transcranial direct current stimulation (tDCS), transcutaneous spinal direct current stimulation (tsDCS), pudendal nerve stimulation, multifidus muscle stimulation, transcutaneous electrical nerve stimulation (TENS), tibial nerve stimulation, among other peripheral nerve or organ stimulation. The IND 112 may additionally or alternatively provide therapies such as radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, or nerve blocks or injections.

In various examples, the electrodes 116 may be distributed in one or more leads of the lead system 114 electrically coupled to the IND 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IND 112 and tissue of the patient. The neurostimulation pulses are each delivered from the IND 112 through a set of electrodes selected from the electrodes 116. In various examples, the neurostimulation pulses may include one or more individually defined pulses, and the set of electrodes may be individually definable by the user for each of the individually defined pulses.

Although the discussion herein with regard to the neuromodulation system 100 focuses on implantable device such as the IND 112, this is meant only by way of example and not limitation. It is within the contemplation of the present inventors and within the scope of this document, that the systems, devices, and methods discussed herein may also be used for pain management via subcutaneous medical devices, wearable medical devices (e.g., wrist watch, patches, garment- or shoe-mounted device, etc.), or other external medical devices, or a combination of implantable, wearable, or other external devices. The therapy, such as electrostimulation or medical therapies, may be used to treat various neurological disorders other than pain, which by way of example and not limitation may include epilepsy, obsessive compulsive disorder, tremor, Parkinson's disease, or dystonia, among other movement and affective disorders.

The external system 130 may be communicated with the IND 112 via a communication link 120. The external system 130 may include a dedicated hardware/software system such as a programmer, a remote server-based patient management system, or alternatively a system defined predominantly by software running on a standard personal computer. The external system 130 may be configured to control the operation of the IND 112, such as to program a neuromodulation therapy. The external system 130 may additionally receive via the communication link 120 information acquired by IND 112, such as one or more sensor signals including information corresponding to pain-induced emotional or psychological expression. In an example, the external system 130 may determine a pain score based on the pain-induced emotional or psychological expression such as received from the IND 112, and program the IND 112 to deliver pain therapy in a closed-loop fashion. Examples of the external system and neurostimulation based on pain score are discussed below, such as with reference to FIGS. 2-3.

The communication link 120 may include one or more communication channels and intermediate devices between the external system and the IND, such as a wired link, a telecommunication link such as an internet connection, or a wireless link such as one or more of an inductive telemetry link, a radio-frequency telemetry link. The communication link 120 may provide for data transmission between the IND 112 and the external system 130. The transmitted data may include, for example, real-time sensor signals acquired by and stored in the IND 112, therapy history data, data indicating device operational status of the IND 112, one or more programming instructions to the IND 112 which may include configurations for sensing physiologic signal or stimulation commands and stimulation parameters, or device self-diagnostic test, among others. In some examples, the IND 112 may be coupled to the external system 130 further via an intermediate control device, such as a handheld external remote control device to remotely instruct the IND 112 to generate electrical stimulation pulses in accordance with selected stimulation parameters produced by the external system 130.

Portions of the IND 112 or the external system 130 may be implemented using hardware, software, firmware, or combinations thereof. Portions of the IND 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
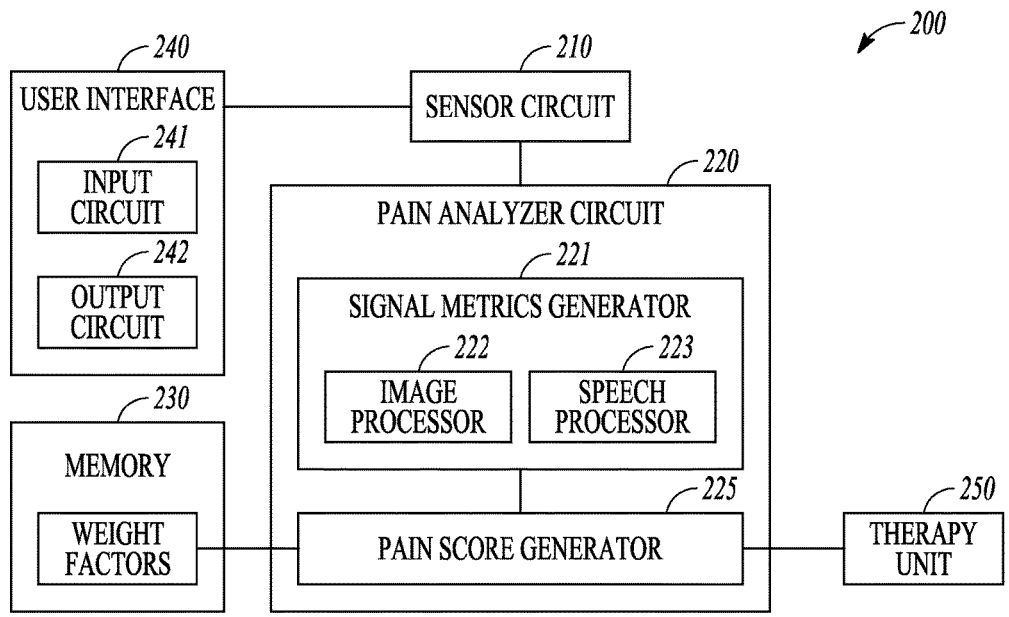
FIG. 2 illustrates, by way of example and not limitation, a block diagram of a pain management system.

FIG. 2 illustrates, by way of example and not limitation, an example of a pain management system 200, which may be an embodiment of the neuromodulation system 100. The pain management system 200 may assess pain in a subject using signals indicative of patient emotional or psychological reaction to pain, and program a pain therapy based on the pain assessment. As illustrated in FIG. 2, the pain management system 200 may include a sensor circuit 210, a pain analyzer circuit 220, a memory 230, a user interface 240, and a therapy unit 250.

The sensor circuit 210 may be coupled to one or more sensors to sense from the patient signals indicative of patient emotional reaction to pain, which may include patient facial, vocal, or behavioral expression signals. The sensor circuit 210 may include sense amplifier circuit that may pre-process the sensed signals, including, for example, amplification, digitization, filtering, or other signal conditioning operations. The sensors may be ambulatory (e.g., implantable or wearable) sensors associated with the patient, stationary sensors mounted in a room or attached to furniture to detect patient motor activities or emotional expressions when the patient enters into, or remains within, an environment of patient daily life. The sensors may alternatively be disposed in a mobile device such as a smart phone, a wearable health monitor, a tablet, a laptop computer, or other types of portable computerized device.

In an example, the sensor circuit 210 may be coupled a camera to capture a facial image or a video sequence of the patient. In another example, the sensor circuit 210 may be coupled a microphone and a voice recorder to record voice or a speech of the patient. In yet another example, the sensor circuit 210 may be coupled to an accelerometer sensor configured to sense skull vibration during patient speech. Speech may induce vibrations conducted through the bones of the skull. Abnormality in speech motor control, which is indicative of occurrence of a pain episode or worsening pain, may correspond to a characteristic skull vibration pattern. The skull vibration pattern may be correlated to the pain type or pain intensity. In an example, the accelerometer is an implantable sensor on a lead surgically placed in or on the skull and coupled to the IND 112, or an injectable wireless sensor in communication with the IND 112. In another example, the accelerometer is a wearable sensor such as disposed on a headgear, where the accelerometer may be in secure contact with patient skull when the headgear is worn on the patient head. The captured facial image, and/or the recorded speech, may be processed to produce respective information corresponding to facial or vocal expression. Examples of the sensors configured to detect emotional expressions of a patient are discussed below, such as with reference to FIG. 4.

In various examples, in addition to the information corresponding to emotional expressions such as facial or vocal expressions, the sensor circuit 210 may further be coupled to one or more sensors to sense a physiological or functional signal. Various physiological signals, such as cardiac, pulmonary, neural, or biochemical signals may demonstrate characteristic signal properties in response to an onset, intensity, severity, duration, or patterns of pain. Examples of the physiological signals may include an electrocardiograph (ECG), intracardiac electrogram, gyrocardiography, magnetocardiography, a heart rate signal, a heart rate variability signal, a cardiovascular pressure signal, a heart sounds signal, a respiratory signal, a thoracic impedance signal, a respiratory sounds signal, or blood chemistry measurements or expression levels of one or more biomarkers. Examples of the functional signals may include patient posture, gait, balance, or physical activity signals, among others. The sensor circuit may sense the functional signals using a motion sensor, such as an accelerometer, gyroscope (which may be a one-, two-, or three-axis gyroscope), magnetometer (e.g., a compass), inclinometers, goniometers, electromagnetic tracking system (ETS), or a global positioning system (GPS) sensor, among others. Detailed description of functional signals for use in pain characterization are disclosed in commonly assigned U.S. Provisional Patent Application Ser. No. 62/445,075, entitled "PAIN MANAGEMENT BASED ON FUNCTIONAL MEASUREMENTS", the disclosures of which are incorporated herein by reference. Commonly assigned U.S. Provisional Patent Application Ser. No. 62/445,053, entitled "PAIN MANAGEMENT BASED ON CARDIOVASCULAR PARAMETERS" describes cardiovascular parameters such as arterial pulsatile activity and electrocardiography for use in pain analysis, the disclosure of which is incorporated herein by reference in its entirety. Commonly assigned U.S. Provisional Patent Application Ser. No. 62/445,061, entitled "PAIN MANAGEMENT BASED ON BRAIN ACTIVITY MONITORING" describes information of brain activity for use in pain analysis, the disclosure of which is incorporated herein by reference in its entirety. Commonly assigned U.S. Provisional Patent Application Ser. No. 62/445,061, entitled "PAIN MANAGEMENT BASED ON BRAIN ACTIVITY MONITORING" describes information of brain activity for use in pain analysis, the disclosure of which is incorporated herein by reference in its entirety. Commonly assigned U.S. Provisional Patent Application Ser. No. 62/445,069, entitled "PAIN MANAGEMENT BASED ON RESPIRATION-MEDIATED HEART RATES" describes information of respiration-mediated heart rate for use in pain analysis, the disclosure of which is incorporated herein by reference in its entirety. Commonly assigned U.S. Provisional Patent Application Ser. No. 62/445,092, entitled "PAIN MANAGEMENT BASED ON MUSCLE TENSION MEASUREMENTS" describes measurements of patient muscle tension including electromyography for use in pain analysis, the disclosure of which is incorporated herein by reference in its entirety. One or more of these additional signals or measurements may be used by the pain analyzer circuit 220 to generate a pain score.

The pain analyzer circuit 220 may generate a pain score based on at least the information corresponding to the emotional reaction to pain detected by the sensor circuit 210. The pain analyzer circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The pain analyzer circuit 220 may include circuit sets comprising one or more other circuits or sub-circuits that may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the pain analyzer circuit 220 may include a signal metrics generator 221 and a pain score generator 225. The signal metrics generator 221 may generate from the sensed signals one or more signal metrics. The signal metrics may include statistical parameters extracted from the sensed signal, such as signal mean, median, or other central tendency measures or a histogram of the signal intensity, among others. The signal metrics may additionally or alternatively include morphological parameters such as maximum or minimum within a specified time period, positive or negative slope or higher order statistics, or signal power spectral density at a specified frequency range, among other morphological parameters. The signal metrics may additionally include timing information such as a time interval between a first characteristic point in one signal and a second characteristic point in another signal.

By way of example and as illustrated in FIG. 2, the signal metrics generator 221 may include one or more of an image processor 222 and a speech processor 223. The image processor 222 may be configured to analyze the captured facial image during a pain episode, and generate a facial expression metric from the captured facial image. In an example, the image processor 222 may process the facial image by performing one or more of image segmentation, transformation, feature extraction, and pattern recognition. The image segmentation includes partitioning the facial image into different segments representing specific facial landmarks. The transformation includes mathematically transforming the image data (e.g., digital image data) into representations in a temporal, spatial, or frequency domain to facilitate feature extraction. The feature extraction includes extracting, from the processed image segments, one or more facial expression metrics of a facial landmark, such as an eye, a nose, a mouth, or a cheek. By way of example and not limitation, the facial expression metrics may include, for example, metrics of lowered brows, raised cheeks, tightened eyelids, a raised upper lip, an open mouth, or closed eyes, among other characteristic facial expressions indicative of emotional reaction to pain. In some examples, the facial expression metrics may be extracted from a sequence of facial images or a facial video. The facial expression metrics may include spatial, temporal, or spatiotemporal change, rate of change, or other motion descriptions of a facial landmark.

The speech processor 223 may be configured to analyze the recorded voice or speech, and generate a vocal expression metric from the recorded voice or speech. Patient with chronic pain may present with impaired cognitive function, emotional and psychological distress, depression, and motor control impairment. Chronic pain can directly or indirectly result in abnormality in speech motor control. The speech processor 223 may process the recorded voice or speech by performing one or more of speech segmentation, transformation, feature extraction, and pattern recognition. The speech segmentation may include partitioning the recorded speech or voice into different segments representing specified speech tasks such as a group of words, syllables, or phonemes. The transformation includes mathematically transforming the speech data (e.g., digital speech signal) into representations in a specific temporal or frequency domain to facilitate feature extraction or recognition. By feature extraction, one or more vocal expression metrics may be generated from the processed speech segments using one of speech recognition algorithms, such as a neural network model, logistic regression model, generalized linear model (GLM), a Hidden-Markov model, a dynamic time warping, among other supervised or unsupervised machine learning algorithms.

The vocal expression metric may include speech motor control features corresponding to production of voice and speech, and speech content-based features based on contents of patient speech regarding intensity, duration, or pattern of pain sensation. Examples of the speech motor control features may include speed, volume, pitch, inclination, regularity, and degree of coordination during speech. In an example, the vocal expression metrics may be measured during a supervised session when the patient rapidly pronounces specific syllables or words, an activity that requires fine coordinated movement of jaw, lips, and anterior and posterior tongue. Speech motor slowness, such as slower syllable pronunciation or an increased variability of accuracy in syllable pronunciation, may be correlative to intensity or duration of pain.

Metrics of emotional expressions such as facial or vocal expression metrics may include time-domain features such as signal magnitude or variance, frequency-domain features such as power spectra at specified frequency bands, spectral entropy, frequency modulation of speech, or other transformed-domain features such as obtained from wavelet decomposition or speech signal filtering through a filter bank. In some examples, the feature extraction and recognition may include reducing the feature dimensionality through feature space projection such as a principal component analysis (PCA). Examples of the signal metrics for pain quantification are discussed below, such as with reference to FIG. 4.

The pain score generator 225 may generate a pain score using the measurements of the signal metrics generated by the signal metrics generator 221. The pain score can be represented as a numerical or categorical value that quantifies the patient's overall pain symptom. In an example, a composite pain score may be generated using a combination of a plurality of facial expression metrics, a combination of a plurality of vocal expression metrics, or a combination of at least one facial expression metric and at least one vocal expression metric. In some examples, the pain score generator 225 may use one or more signals metrics generated from a physiological or functional signal, in addition to the facial or vocal expression metrics, to generate the pain score. The signal metrics may be weighted by their respective weight factors before being combined. The combination can be linear or nonlinear. The pain score generator 225 may compare the composite signal metric to one or more threshold values or range values, and assign a corresponding pain score (such as numerical values from 0 to 10) based on the comparison.

In another example, the pain score generator 225 may compare the signal metrics to their respective threshold values or range values, assign corresponding signal metric-specific pain score based on the comparison, and compute a composite pain score using a linear or nonlinear fusion of the signal metric-specific pain scores weighted by their respective weight factors. In an example, the threshold can be inversely proportional to signal metric's sensitivity to pain. A signal metric that is more sensitive to pain may have a corresponding lower threshold and a larger metric-specific pain score, thus plays a more dominant role in the composite pain score than another signal metric that is less sensitive to pain. Examples of the fusion algorithm may include weighted averages, voting, decision trees, or neural networks, among others. The pain score generated by the pain score generator 225 may be output to a system user or a process.

In some example, the pain score generator 225 may generate a metric-specific pain score based on a comparison of the facial or vocal expression metric to a template Ti. The template Ti may be an individualized or population-based representative facial or vocal expression pattern when the patient experiences pain. The pain score generator 225 may compute a similarity measure between the facial or vocal expression metric and their respective template, and determine the metric-specific pain score based on the similarity measure. In an example, the pain score generator 225 may generate a facial expression metric-specific pain score $X_{Fi}$ based on a comparison of (a) the facial expression metric Fi of a specified facial landmark and (b) a facial image template $TF_i$ of the same specified facial landmark. The facial image template Ti may be formed from an individual patient baseline, such as an image of the specified facial landmark when the patient experiences a known pain episode. Alternatively, the facial image template TFi may be formed from a population database, and represent a universal image of the specified facial landmark when the patients experience pain. The facial image template TFi thus formed can be referred to as a representative "pain template" of the specified facial landmark. Alternatively, the facial image template TFi may be a "pain-free template" formed using individualized or population-based images when the patient experiences no known pain. A similarity measure between the facial expression metric Fi and the template TFi, denoted by S(Fi, TFi), may be computed. Examples of the similarity measure may include distance in a normed vector space (such as L1 norm, L2 norm or Euclidian distance, and infinite norm), correlation coefficient, mutual information, or ratio image uniformity, among others.

The metric-specific pain score $X_{Fi}$ may be determined as a function of the similarity measure S(Fi,TFi), that is, $X_{Fi}$=f (S(Fi, TFi)), where f is linear or nonlinear function. In an example, the $X_{Fi}$ may be proportional to the similarity measure S(Fi,TFi), that is, $X_{Fi}$=k*(S(Fi, TFi), where k is a positive coefficient. A higher pain score may be assigned for the facial expression metric Fi if it highly resembles the individualized or population-based "pain template." In a similar fashion, the pain score generator 225 may generate additional facial expression metric-specific pain score $X_{Fj}$ pertaining to a different facial expression metric Fj. The metrics Fi and Fj may be selected from, for example, lowered brows, raised cheeks, tightened eyelids, a raised upper lip, an open mouth, or closed eyes, among other characteristic facial expressions indicative of emotional effect of pain. The pain score generator 225 may generate a composite pain score X such as a weighted combination of the metric-specific pain scores $X_{Fi}$ and $X_{Fj}$.

In a similar fashion, the pain score generator 225 may compute vocal expression metric-specific pain score $X_{Vi}$ and $X_{Vj}$ based on similarity measures between vocal expression metrics (e.g., Vi and Vj) and their respective speech templates (e.g., TSi and TSj), and compute composite pain score X such as a weighted combination of the metric-specific pain scores $X_{Vi}$ and $X_{Vj}$. In some examples, the composite pain score X may be computed as weighted combination of both the metric-specific pain scores pertaining to facial image metrics (e.g., $X_{Fi}$ and $X_{Fj}$) and the metric-specific pain scores pertaining to vocal expression metrics (e.g., $X_{Vi}$ and $X_{Vj}$).

The memory 230 may be configured to store sensor signals or signal metrics such as generated by the sensor circuit 210 and the signal metrics generator 221, and the pain scores such as generated by the pain score generator 225. Data storage at the memory 230 may be continuous, periodic, or triggered by a user command or a specified event. In an example, as illustrated in FIG. 2, the memory 230 may store weight factors, which may be used by the pain score generator 225 to generate the pain score. The weight factors may be provided by a system user, or alternatively be automatically determined or adjusted such as based on the corresponding signal metrics' reliability in representing an intensity of the pain. Examples of the automatic weight factor generation are discussed below, such as with reference to FIG. 3.

The user interface 240 may include an input circuit 241 and an output unit 242. In an example, at least a portion of the user interface 240 may be implemented in the external system 130. The input circuit 241 may enable a system user to program the parameters used for sensing the image, speech, or other physiological or functional signals, generating signal metrics, or generating the pain score. The input circuit 241 may be coupled to one or more input devices such as a keyboard, on-screen keyboard, mouse, trackball, touchpad, touch-screen, or other pointing or navigating devices. In some example, the input circuit 241 may be incorporated in a mobile device such as a smart phone or other portable electronic device with a mobile application ("App"). The mobile App may enable a patient to provide self-reported pain episode and quantified pain scales. In an example, the input circuit 241 may enable a user to confirm, reject, or edit the programming of the therapy unit 250, such as parameters for electrostimulation, as to be discussed in the following.

The output unit 242 may include a display to present to a system user such as a clinician the pain score. The output unit 242 may also display information including the sensor signals, trends of the signal metric, or any intermediary results for pain score calculation such as the signal metric-specific pain scores. The information may be presented in a table, a chart, a diagram, or any other types of textual, tabular, or graphical presentation formats, for displaying to a system user. The presentation of the output information may include audio or other human-perceptible media format. In an example, the output unit 242 may generate alerts, alarms, emergency calls, or other forms of warnings to signal the system user about the pain score.

The therapy circuit 250 may be configured to deliver a therapy to the patient in response to the pain score. In an example, the therapy circuit 250 may include an electrostimulator configured to generate electrostimulation energy to treat pain. In an example, the electrostimulator may deliver spinal cord stimulation (SCS) via electrodes electrically coupled to the electrostimulator. The electrodes may be surgically placed at a region at or near a spinal cord tissue, which may include, by way of example and not limitation, dorsal column, dorsal horn, spinal nerve roots such as the dorsal nerve root, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator may additionally or alternatively deliver electrostimulation to other target tissues such as peripheral nerves tissues. In an example, the electrostimulator may deliver transcutaneous electrical nerve stimulation (TENS) via detachable electrodes that are affixed to the skin.

The therapy circuit 250 may additionally or alternatively include a drug delivery system, such as an intrathecal drug delivery pump that may be surgically placed under the skin, which may be programmed to inject medication or biologics through a catheter to the area around the spinal cord. Other examples of drug delivery system may include a computerized patient-controlled analgesia pump that may deliver the prescribed pain medication to the patient such as via an intravenous line. In some examples, the therapy circuit 250 may be delivered according to the pain score received from the pain score generator 225.

Figure 3:
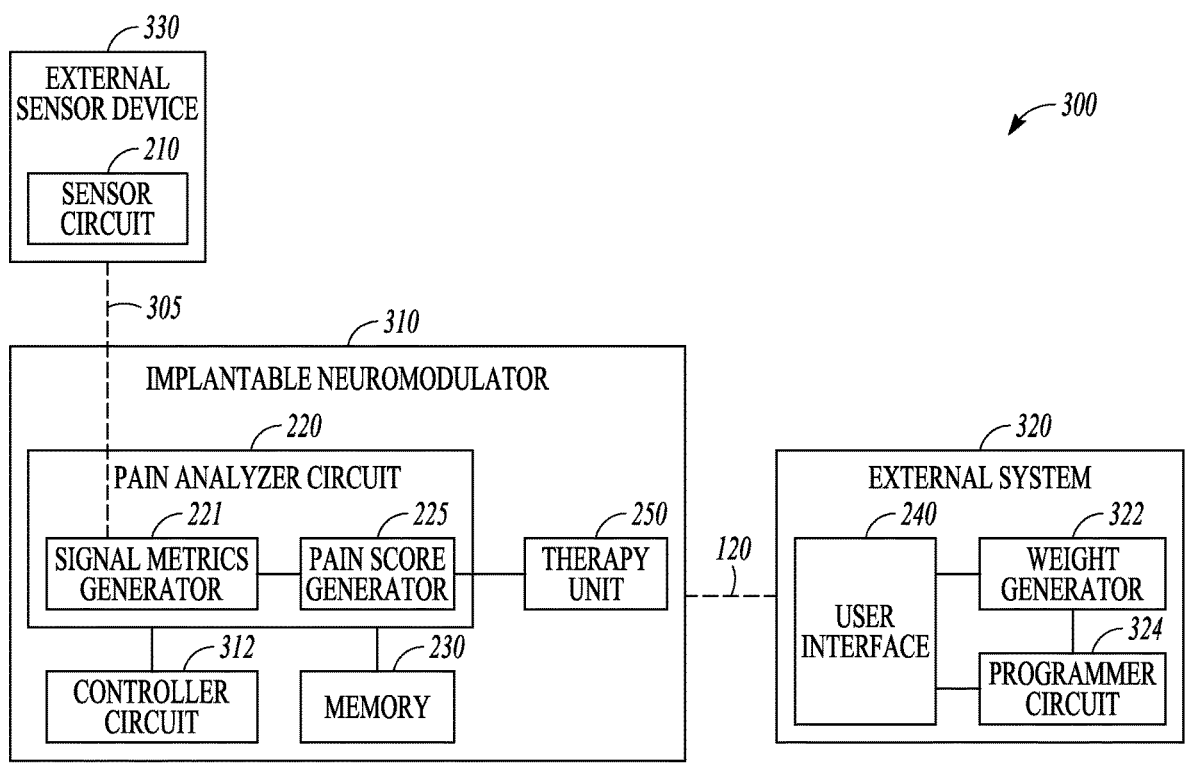
FIG. 3 illustrates, by way of example and not limitation, a block diagram of another pain management system.

FIG. 3 illustrates, by way of example and not limitation, another example of a pain management system 300, which may be an embodiment of the neuromodulation system 100 or the pain management system 200. The pain management system 300 may include an implantable neuromodulator 310 and an external system 320 which may be, respectively, embodiments of the IND 112 and the external system 130 as illustrated in FIG. 1. The external system 320 may be communicatively coupled to the implantable neuromodulator 310 via the communication link 120. The pain management system 300 may additionally include an external sensor device 330 coupled to the implantable neuromodulator 310 via a communication link 305.

The external sensor device 330 may include the sensor circuit 210, which may be coupled to one or more sensors to detect physiological or functional signals or information corresponding to emotional expressions of a patient, as previously discussed with reference to FIG. 1. The external sensor device 330 may be a portable device, such as an implantable or wearable patient monitor, a portal electronic device such as a smart phone, a smart wearable, a portable health monitor, a tablet, a laptop computer, or other types of portable computerized device. In an example, the external sensor device 330 may include a camera configured to capture a facial image of the patient, or a microphone and a voice recorder to record voice or speech of the patient. The external sensor device 330 may be a stationary device such as positioned in a room or attached to furniture to detect patient motor activities or emotional expressions when the patient enters, or remains within, an environment within the scope of surveillance of the stationary sensor. In some examples, the external sensor device 330 may include devices configured to receive patient self-reported pain perception, such as a patient diary via text and voice, or external conditions such as weather, temperature, patient stress level, or recent medication intake, among others.

The implantable neuromodulator 310 may be communicatively coupled to the external sensor device 330 via the communication link 305. Examples of the communication link 305 may include a wired connection including universal serial bus (USB) connection, or otherwise cables coupled to communication interfaces on both the mobile device 400 and the AMD 302. Alternatively, the communication link 302 may include a wireless connection including Bluetooth protocol, Ethernet, IEEE 802.11 wireless, an inductive telemetry link, or a radio-frequency telemetry link, among others. The sensor signals acquired by the external sensor device 330 may be transmitted to the implantable neuromodulator 310 continuously, periodically, or in response to a data transmission request from the implantable neuromodulator 310. As illustrated in FIG. 3, the implantable neuromodulator 310 may include several components of the pain management system 200 as illustrated in FIG. 2, including the pain analyzer circuit 220, the memory 230, and the therapy unit 250. As discussed with reference to FIG. 2, the pain analyzer circuit 220 includes the pain score generator 225 that determines a pain score using weight factors stored in the memory 230 and the signal metrics from the signal metrics generator 221 which may also be included in the pain analyzer circuit 220. In some examples, the signal metrics generator 221 may be implemented in the external sensor device 330. The signal metrics, such as facial or vocal expression metrics, may be transmitted to the implantable neuromodulator 310 via the communication link 305.

The implantable neuromodulator 310 may include a controller circuit 312, coupled to the therapy unit 250, which controls the generation and delivery of pain therapy, such as neurostimulation energy. The controller circuit 312 may control the generation of electrostimulation pulses according to specified stimulation parameters. The stimulation parameters may be provided by a system user. Alternatively, the stimulation parameters may be automatically determined based on the intensity, severity, duration, or pattern of pain, which may be subjectively described by the patient or automatically quantified based on the physiological or functional signals sensed by the sensor circuit 210. For example, when a patient-described or sensor-indicated quantification exceeds a respective threshold value or falls within a specified range indicating elevated pain, the electrostimulation energy may be increased to provide stronger pain relief. Increased electrostimulation energy may be achieved by programming a higher pulse intensity, a higher frequency, or a longer stimulation duration or "on" cycle, among others. Conversely, when a patient-described or sensor-indicated pain quantification falls below a respective threshold value or falls within a specified range indicating no pain or mild pain, the electrostimulation energy may be decreased. The controller circuit 312 may also adjust stimulation parameters to alleviate side effects introduced by the electrostimulation of the target tissue.

Additionally or alternatively, the controller circuit 312 may control the therapy unit 250 to deliver electrostimulation pulses via specified electrodes. In an example of pain management via SCS, a plurality of segmented electrodes, such as the electrodes 116, may be distributed in one or more leads. The controller circuit 312 may configure the therapy unit 250 to deliver electrostimulation pulses via a set of electrodes selected from the plurality of electrodes. The electrodes may be manually selected by a system user, or automatically selected based on the pain score.

The implantable neuromodulator 310 may receive the information about electrostimulation parameters and the electrode configuration from the external system 320 via the communication link 120. Additional parameters associated with operation of the therapy unit 250, such as battery status, lead impedance and integrity, or device diagnostic of the implantable neuromodulator 310, may be transmitted to the external system 320. The controller circuit 312 may control the generation and delivery of electrostimulation using the information about electrostimulation parameters and the electrode configuration from the external system 320. Examples of the electrostimulation parameters and electrode configuration may include: temporal modulation parameters such as pulse amplitude, pulse width, pulse rate, or burst intensity; morphological modulation parameters respectively defining one or more portions of stimulation waveform morphology such as amplitude of different phases or pulses included in a stimulation burst; or spatial modulation parameters such as selection of active electrodes, electrode combinations which define the electrodes that are activated as anodes (positive), cathodes (negative), and turned off (zero), and stimulation energy fractionalization which defines amount of current, voltage, or energy assigned to each active electrode and thereby determines spatial distribution of the modulation field.

In an example, the controller circuit 312 may control the generation and delivery of electrostimulation in a closed-loop fashion by adaptively adjusting one or more stimulation parameters or stimulation electrode configuration based on the pain score. For example, if the score exceeds the pain threshold (or falls within a specified range indicating an elevated pain), then the first electrostimulation may be delivered. Conversely, if the multi-sensor pain score falls below a respective threshold value (or falls within a specified range indicating no pain or mild pain), then a second pain therapy, such as second electrostimulation may be delivered. The first electrostimulation may differ from the second electrostimulation with respect to at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. In an example, the first electrostimulation may have higher energy than the second electrostimulation, such as to provide stronger effect of pain relief. Examples of increased electrostimulation energy may include a higher pulse intensity, a higher frequency, or a longer stimulation duration or "on" cycle, among others.

The parameter adjustment or stimulation electrode configuration may be executed continuously, periodically at specified time, duration, or frequency, or in a commanded mode upon receiving from a system user a command or confirmation of parameter adjustment. In some examples, the closed-loop control of the electrostimulation may be further based on the type of the pain, such as chronic or acute pain. In an example, the pain analyzer circuit 220 may trend the signal metric over time to compute an indication of abruptness of change of the signal metrics, such as a rate of change of facial or vocal expression metrics. The pain episode may be characterized as acute pain if the signal metric changes abruptly (e.g., the rate of change of the signal metric exceeding a threshold), or as chronic pain if the signal metric changes gradually (e.g., the rate of change of the signal metric falling below a threshold). The controller circuit 312 may control the therapy unit 250 to deliver, withhold, or otherwise modify the pain therapy in accordance with the pain type. For example, incidents such as toe stubbing or bodily injuries may cause abrupt changes in certain signal metrics, but no adjustment of the closed-loop pain therapy is deemed necessary. On the contrary, if the pain analyzer circuit 220 detects chronic pain characterized by gradual signal metric change, then the closed-loop pain therapy may be delivered accordingly.

The external system 320 may include the user interface 240, a weight generator 322, and a programmer circuit 324. The weight generator 322 may generate weight factors used by the pain score generator 225 to generate the pain score. The weight factors may indicate the signal metrics' reliability in representing an intensity of the pain. A sensor metric that is more reliable, or more sensitive or specific to the pain, would be assigned a larger weight than another sensor metric that is less reliable, or less sensitive or specific to the pain. In an example, the weight factors may be proportional to correlations between a plurality of quantified pain scales (such as reported by a patient) and measurements of the measurements of the signal metrics corresponding to the plurality of quantified pain scales. A signal metric that correlates with the pain scales is deemed a more reliable signal metric for pain quantification, and is assigned a larger weight factor than another signal metric less correlated with the quantified pain scales. In another example, the weight generator 322 may determine weight factors using the signal sensitivity to pain. The signal metrics may be trended over time, such as over approximately six months. The signal sensitivity to pain may be represented by a rate of change of the signal metrics over time during a pain episode. The signal sensitivity to pain may be evaluated under a controlled condition such as when the patient posture or activity is at a specified level or during specified time of the day. The weight generator 322 may determine weight factors to be proportional to signal metric's sensitivity to pain.

The programmer circuit 324 may produce parameter values for operating the implantable neuromodulator 310, including parameters for sensing physiological and functional signals and generating signal metrics, and parameters or electrode configurations for electrostimulation. In an example, the programmer circuit 324 may generate the stimulation parameters or electrode configurations for SCS based on the pain score produced by the pain score generator 225. Through the communication link 120, the programmer circuit 324 may continuously or periodically provide adjusted stimulation parameters or electrode configuration to the implantable neuromodulator 210A. By way of non-limiting example and as illustrated in FIG. 3, the programmer circuit 324 may be coupled to the user interface 234 to allow a user to confirm, reject, or edit the stimulation parameters, sensing parameters, or other parameters controlling the operation of the implantable neuromodulator 210A. The programmer circuit 324 may also adjust the stimulation parameter or electrode configuration in a commanded mode upon receiving from a system user a command or confirmation of parameter adjustment.

The programmer circuit 324, which may be coupled to the weight generator 322, may initiate a transmission of the weight factors generated by the weight generator 322 to the implantable neuromodulator 310, and store the weight factors in the memory 230. In an example, the weight factors received from the external system 320 may be compared to previously stored weight factors in the memory 230. The controller circuit 312 may update the weight factors stored in the memory 230 if the received weight factors are different than the stored weights. The pain analyzer circuit 220 may use the updated weight factors to generate a pain score. In an example, the update of the stored weight factors may be performed continuously, periodically, or in a commanded mode upon receiving a command from a user. In various examples, weight factors may be updated using a fusion model. Commonly assigned U.S. Provisional Patent Application Ser. No. 62/445,095, entitled "PATIENT-SPECIFIC CALIBRATION OF PAIN QUANTIFICATION" describes systems and methods for calibrating a fusion model, such as adjusting weights for signal metrics, using a reference pain quantification, the disclosure of which is incorporated herein by reference in its entirety.

In some examples, the pain score may be used by a therapy unit (such as an electrostimulator) separated from the pain management system 300. In various examples, the pain management system 300 may be configured as a monitoring system for pain characterization and quantification without delivering closed-loop electrostimulation or other modalities of pain therapy. The pain characterization and quantification may be provided to a system user such as the patient or a clinician, or to a process including, for example, an instance of a computer program executable in a microprocessor. In an example, the process includes computer-implemented generation of recommendations or an alert to the system user regarding pain medication (e.g., medication dosage and time for taking a dose), electrostimulation therapy, or other pain management regimens. The therapy recommendations or alert may be based on the pain score, and may be presented to the patient or the clinician in various settings including in-office assessments (e.g. spinal cord stimulation programming optimization), in-hospital monitoring (e.g. opioid dosing during surgery), or ambulatory monitoring (e.g. pharmaceutical dosing recommendations).

In an example, in response to the pain score exceeding a threshold which indicates elevated pain symptom, an alert may be generated and presented at the user interface 240 to remind the patient to take pain medication. In another example, therapy recommendations or alerts may be based on information about wearing-off effect of pain medication, which may be stored in the memory 230 or received from the user interface 240. When the drug effect has worn off, an alert may be generated to remind the patient to take another dose or to request a clinician review of the pain prescription. In yet another example, before a pain therapy such as neurostimulation therapy is adjusted (such as based on the pain score) and delivered to the patient, an alert may be generated to forewarn the patient or the clinician of any impending adverse events. This may be useful as some pain medication may have fatal or debilitating side effects. In some examples, the pain management system 300 may identify effect of pain medication addiction such as based on functional and physiological signals. An alert may be generated to warn the patient about effects of medication addiction and thus allow medical intervention.

Figure 4:
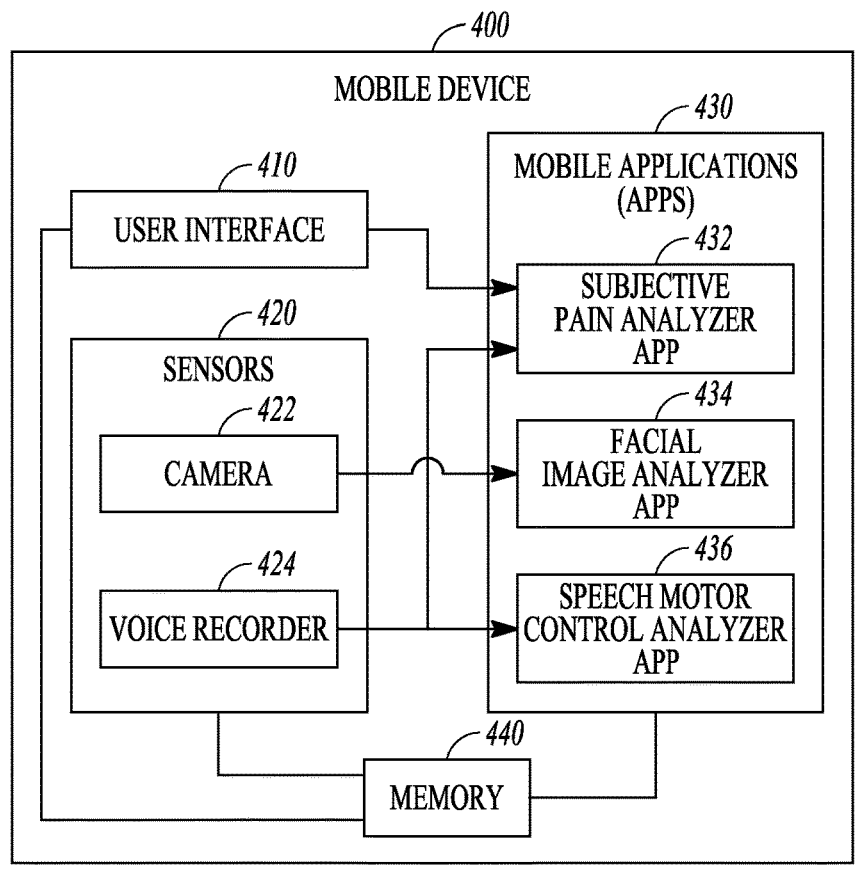
FIG. 4 illustrates, by way of example and not limitation, a block diagram of a mobile device for detecting information corresponding to various emotional expressions indicative of pain.

FIG. 4 illustrates, by way of example and not limitation, a block diagram of a mobile device 400 for detecting information corresponding to various emotional expressions indicative of pain. The mobile device 400, which is an embodiment of the external sensor device 330, may be configured for wireless communication with the implantable neuromodulator 310 and to execute mobile applications ("apps") to detect the facial or vocal expression. Examples of the mobile device 400 may include a smart phone, a wearable device, a portable health monitor, a tablet, a laptop computer, or other types of portable computerized device.

The mobile device 400 may comprise a user interface 410 to receive user input, one or more sensors 420 to sense information corresponding to patient emotional reaction to pain, and a processor configured to execute one or more mobile apps 430 to generate respective facial or vocal expression metrics indicative of pain. The user interface 410 may include an input circuit and a display screen. The input circuit may be coupled an input device such as a keyboard, an on-screen keyboard, a touchpad, or a touch-screen, which enables a user to enter texts when prompted to do so. Patient with chronic pain may present with impaired cognitive function, emotional and psychological distress, or depression, among other disorders. In an example, one or more questions or instructions may be displayed on the screen of the user interface 410. The patient user is prompted to answer the questions or perform acts according to the instructions, such as by entering texts using the input device such as a keyboard or a touchpad. In an example, the patient may be prompted to answer questions such as "How are you feeling today?", "Has your back pain improved?", "Select from the following that best describe your pain." Additionally or alternatively, the subjective pain analyzer circuit 432 may operate in a passive mode by extracting textual description of the pain experience from patient regular text messages entered via the user interface 410. Patient subject description of the pain, including the location, intensity, duration, or pattern of pain may be analyzed by the mobile apps and used in pain score calculation.

The sensors 420 may include one more sensors to sense information corresponding to emotional expressions in reaction to pain. By way of example and not limitation, the sensors 420 may include one or more of a camera 422 configured to capture a facial image of the patient, or a voice recorder 424 configured to record voice or speech of the patient. The mobile device 400 may be coupled to one or more external sensors associated with the patient. In an example, the mobile device 400 may be in a wired or wireless communication with a head-mounted accelerometer configured to sense skull vibration during speech, a signal that is correlative to the motor control of speech.

The sensors 420 may capture respective facial image or video, or speech or voice of the patient when the patient is prompted with questions display on the screen of the user interface. Additionally or alternatively, one or more of the sensors 420 may operate in an unprompted passive mode during patient normal use of the mobile device 400. For example, the camera 422 may capture a facial image or video when the patient stares at the display screen such as when reading an email message or browsing web content. The voice recorder 424 may record a spontaneous speech when the patient answers a phone call or leaves a voice mail.

The mobile apps 430 may be coupled to the use interface 410 and one or more of the sensor 420, and configured to generate facial or vocal expression metrics indicative of pain. By way of example and not limitation, the mobile apps 430 may include a subjective pain analyzer circuit app 432, a facial image analyzer app 434, and a speech motor control analyzer app 436. The subjective pain analyzer circuit app 432 may analyze the patient subjective description of the pain symptoms, which may include patient textual input received via the user interface 410, or the content of patient speech regarding the pain perception received via the voice recorder 424. The subjective pain analyzer circuit 432 may generate a subject pain indicator which may be represented by a numerical or categorical value. In an example, the text or voice communications over a period of time may be stored in the memory 440. The subjective pain analyzer circuit 432 may trend the subjective pain indicator over time using the historical text or voice communications, and generate a trend of worsened subjectively described pain symptom. The subjective pain indicator or the trend thereof may be used by the pain score generator 225 to generate a pain score.

The facial image analyzer app 434 and the speech motor control analyzer app 436 are respective embodiments of software implementations of the image processor 222 and the speech processor 223 as illustrated in FIG. 2. The facial image analyzer app 434 may process the facial image or images of one or more facial landmarks captured by the camera 422, and generate one or more facial expression metrics. The speech motor control analyzer app 436 may process the recorded speech and generate one or more vocal expression metrics corresponding to speech motor control. In some examples, the speech motor control analyzer app 436 may process the skull vibration signal such as sensed by a head-mounted accelerometer, and generate vibration signal metrics that are correlated to the speech motor control. The emotional expression metrics, including one or more of the subjective pain indicators, the facial expression metrics, or the vocal expression metrics, may be transmitted to the implantable neuromodulator 310 via the communication link 305. The pain score generator 225 may generate a pain score using the emotional expression metrics, such as described previously with reference to FIG. 3.

Figure 5:
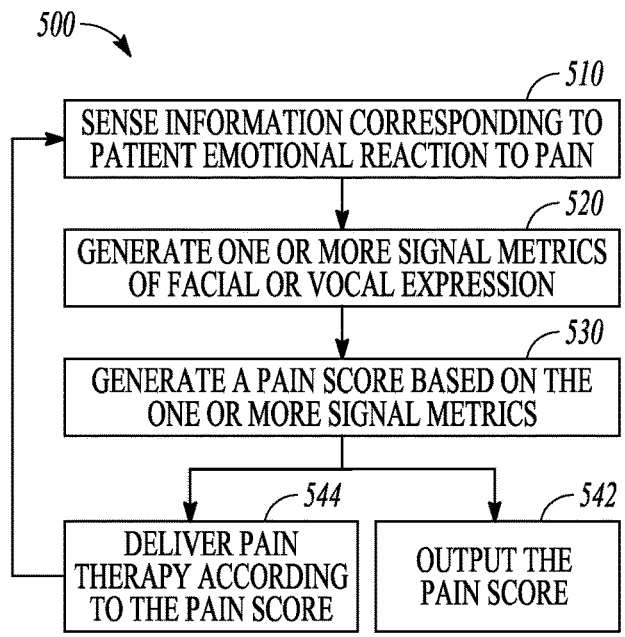
FIG. 5 illustrates, by way of example and not limitation, a method for managing pain of a patient.

FIG. 5 illustrates, by way of example and not limitation, a method 500 for managing pain of a patient. The method 500 may be implemented in a medical system, such as the pain management system 200 or 300. In an example, at least a portion of the method 500 may be executed by a neuromodulator device (IND) such as the implantable neuromodulator 310. In an example, at least a portion of the method 500 may be executed by an external programmer or remote server-based patient management system, such as the external system 320 that are communicatively coupled to the IND. The method 500 may be used to provide neuromodulation therapy to treat chronic pain or other disorders.

The method 500 begins at step 510, where information corresponding emotional expressions, such as facial, vocal, or behavioral expressions, may be sensed from the patient. Chronic pain may have emotional or psychological effects. Patients with chronic pain may experience emotional and psychological distress, and present with characteristic facial expressions, and changes in vocal or behavioral expressions as a result of abnormalities in neurological or psychomotor functioning. Monitoring patient emotional expressions may provide an objective assessment of pain, and may be used to improve pain therapy efficacy.

Information corresponding to facial expression may include images or video sequence captured using a camera. Information corresponding to vocal expression may include speech signals captured using a microphone and a voice recorder. The information corresponding to patient emotional reaction to pain may be sensed using one or more implantable, wearable, or stationary sensors, or one or more sensors disposed in a mobile device, such as a smart phone, a wearable health monitor, a tablet, a laptop computer, or other types of portable computerized device. In an example, the camera or the voice recorder may be disposed in a mobile device, as illustrated in FIG. 4. In some examples, information corresponding to vocal expression sensed at 510 may include skull vibration signals during patient speech, such as sensed using an accelerometer sensor implanted in or worn on the patient skull. Speech-induced vibration may be conducted through the bones of the skull. When in chronic pain, a patient may present with characteristic voice or speech pattern, which may result in characteristic skull vibrations signals. The skull vibration signal may be correlated to the pain intensity or duration.

In some examples, in addition to the information corresponding to emotional expressions such as facial or vocal expressions, one or more physiological or functional signals may also be sensed at 510. Various physiological signals, such as cardiac, pulmonary, neural, or biochemical signals may demonstrate characteristic signal properties in response to an onset, intensity, severity, duration, or patterns of pain. Examples of the physiological signals may include an electrocardiograph (ECG) or intracardiac electrogram, a heart rate signal, a heart rate variability signal, a cardiovascular pressure signal, a heart sounds signal, a respiratory signal, a thoracic impedance signal, a respiratory sounds signal, or blood chemistry measurements or expression levels of one or more biomarkers. Examples of the functional signals may include patient posture, gait, balance, or physical activity signals, among others.

At 520, a plurality of signal metrics may be generated from the sensed information corresponding to emotional expressions. The signal metrics may include statistical, morphological, or temporal metrics. Metrics of emotional expressions may include time-domain features such as signal magnitude or variance, frequency-domain features such as power spectra at specified frequency bands, spectral entropy, frequency modulation of speech, or other transformed-domain features such as obtained from wavelet decomposition or speech signal filtering through a filter bank. In some examples, the signal metrics may be projected onto specific direction on the feature space for dimensionality reduction, such as by using principal component analysis (PCA).

In an example, at 520, the facial image may be processed, including one or more of image segmentation, transformation, feature extraction, and pattern recognition. From the processed facial image, one or more facial expression metrics of a facial landmark, such as an eye, a nose, a mouth, or a cheek, may be extracted, such as by using the image processor 222, or by executing an mobile application such as the facial image analyzer app 434 implemented in the mobile device 300. Examples of the facial expression metrics may include lowered brows, raised cheeks, tightened eyelids, a raised upper lip, an open mouth, or closed eyes, among other characteristic facial expressions indicative of emotional effect of pain. The facial expression metrics may include spatial, temporal, or spatiotemporal change, rate of change, or other motion descriptions of the facial landmark appearance.

In another example, the recorded voice or speech may be processed at 520, including one or more of speech segmentation, transformation, feature extraction, and pattern recognition. From the processed voice or speech signal, one or more vocal expression metrics corresponding to speech motor control may be extracted, such as by using the speech processor 223, or by executing an mobile application such as the speech motor control analyzer app 436 implemented in the mobile device 300. Examples of the vocal expression metrics related to speech motor control may include speed, volume, pitch, inclination, regularity, and degree of coordination during speech. In some examples, the vocal expression metrics may be measured during a supervised session when the patient rapidly pronounces specific syllables or words that requires fine coordinated movement of jaw, lips, and anterior and posterior tongue. Speech motor slowness such as slower syllable pronunciation, or an increased variability of accuracy in syllable pronunciation, may indicate intensity or duration of pain.

At 530, a pain score may be generated using the measurements of the signal metrics. The pain score may be generated using a combination of a plurality of facial expression metrics, a combination of a plurality of vocal expression metrics, or a combination of at least one facial expression metric and at least one vocal expression metric. In some examples, one or more signal metrics generated from a physiological or functional signal may additionally be used to generate the pain score. The pain score may be represented as a numerical or categorical value that quantifies overall pain quality in the subject. In an example, a composite signal metric may be generated using a linear or nonlinear combination of the signal metrics respectively weighted by weight factors. The composite signal metric may be categorized as one of a number of degrees of pain by comparing the composite signal metric to one or more threshold values or range values, and a corresponding pain score may be assigned based on the comparison.

In another example, each signal metric may be compared to a respectively specified threshold or range values and a corresponding signal metric-specific pain score may be determined. In some example, a metric-specific pain score based on a comparison of the facial or vocal expression metric to a template that represents individualized or population-based representative facial or vocal expression pattern when the patient undergoes pain. The metric-specific pain score may be determined based on a similarity measure between facial or vocal expression metric and the respective template. Examples of the similarity measure may include distance in a normed vector space (such as L1 norm, L2 norm or Euclidian distance, and infinite norm), correlation coefficient, mutual information, or ratio image uniformity, among others.

A composite pain score may be generated using a linear or nonlinear fusion of the signal metric-specific pain scores each weighted by their respective weight factors. Examples of the fusion algorithm may include decision trees, voting, weighted averages, or neural networks, among others. In some examples, the pain score may be computed using a subset of the signal metrics selected based on their temporal profile of pain response. Signal metrics with quick pain response (or a shorter transient state of response) may be selected to compute the pain score during a pain episode. Signal metrics with slow or delayed pain response (or a longer transient state of response before reaching a steady state) may be used to compute the pain score after an extended period following the onset of pain such as to allow the signal metrics to reach steady state of response.

At 542, the pain score may be output to a user or to a process, such as via the output unit 242 as illustrated in FIG. 2. The pain score, including the composite pain score and optionally together with metric-specific pain scores, may be displayed on a display screen. Other information, such as the facial image or video sequence or recorded voice or speech, and the signal metrics generated therefrom, may also be output for display or for further processing. In some examples, alerts, alarms, emergency calls, or other forms of warnings may be generated to signal the system user about occurrence of a pain episode or aggravation of pain as indicated by the pain score.

The method 500 may include, at 544, an additional step of delivering a pain therapy to the patient according to the pain score. The pain therapy may include electrostimulation therapy, such as spinal cord stimulation (SCS) via electrodes electrically coupled to the electrostimulator. The SCS may be in a form of stimulation pulses that are characterized by pulse amplitude, pulse width, stimulation frequency, duration, on-off cycle, waveform, among other stimulation parameters. Other electrostimulation therapy, such as one or a combination of DBS, FES, VNS, TNS, or PNS at various locations, may be delivered for pain management. The pain therapy may additionally or alternatively include a drug therapy such as delivered by using an intrathecal drug delivery pump.

In various examples, the pain therapy (such as in the form of electrostimulation or drug therapy) may be delivered in a closed-loop fashion. Therapy parameters, such as stimulation waveform parameters, stimulation electrode combination and fractionalization, drug dosage, may be adaptively adjusted based at least on the pain score. The pain-relief effect of the delivered pain therapy may be assessed based on the signal metrics such as the cardiovascular parameters, and the therapy may be adjusted to achieve desirable pain relief. The therapy adjustment may be executed continuously, periodically at specified time, duration, or frequency, or in a commanded mode upon receiving from a system user a command or confirmation of parameter adjustment. In an example, if the pain score exceeds the pain threshold (or falls within a specified range indicating an elevated pain), then the first electrostimulation may be delivered. Conversely, if the composite pain score falls below a respective threshold value (or falls within a specified range indicating no pain or mild pain), then a second pain therapy, such as second electrostimulation may be delivered. The first electrostimulation may differ from the second electrostimulation with respect to at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. The method 500 may proceed at 510 to sense information corresponding to emotional expressions in response to the therapy delivered at 544. In some examples, the responses of the signal metrics to pain therapy delivered at 544 may be used to gauge composite pain score computation such as by adjusting the weight factors. In an example, weight factors may be determined and adjusted via the weight generator 322 as illustrated in FIG. 3, to be proportional to signal metric's sensitivity to pain.

Figure 6:
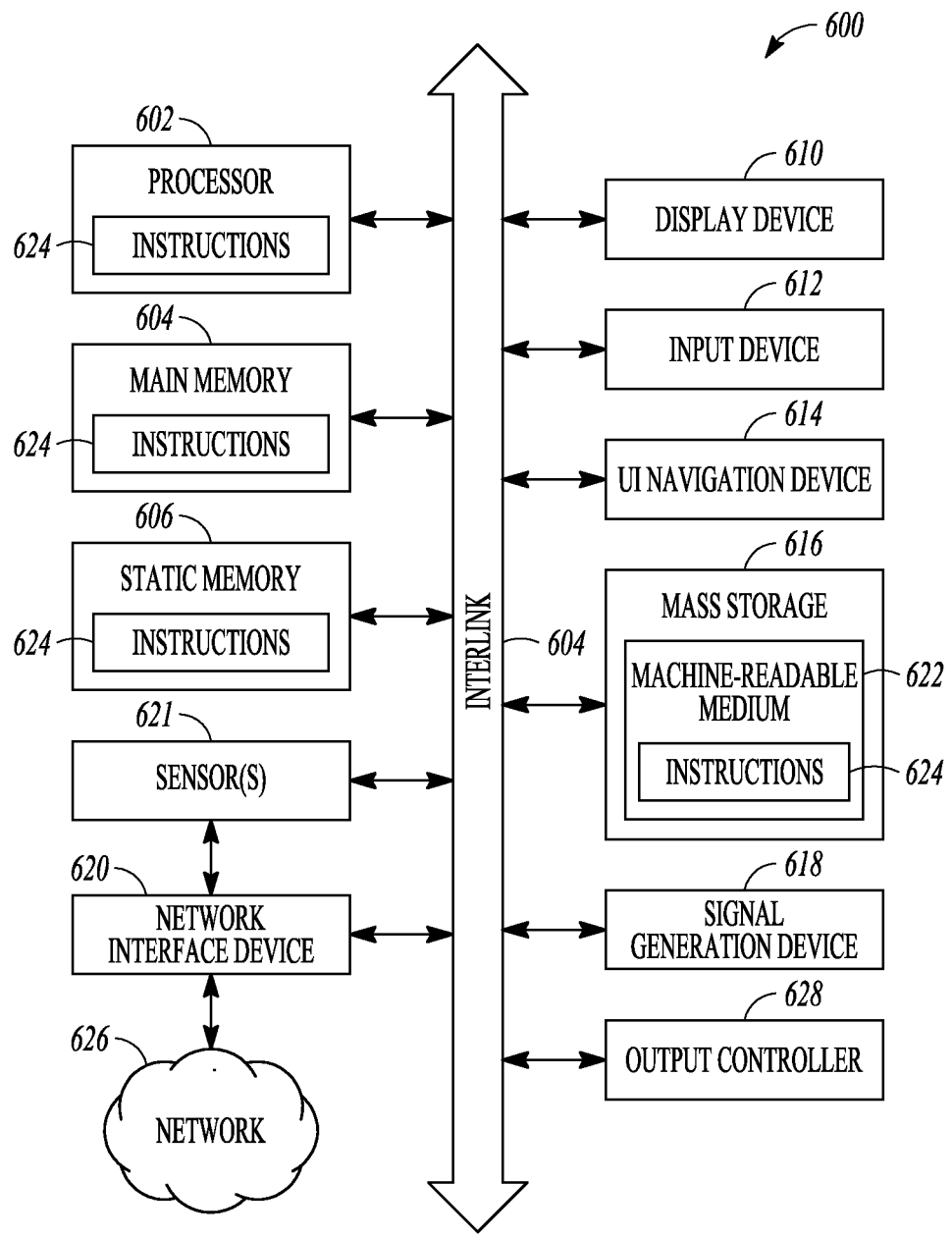
FIG. 6 illustrates, by way of example and not limitation, a block diagram of an example machine upon which any one or more of the techniques discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A method of providing neuromodulation therapy to a patient via a medical-device system, the method comprising:
   receiving information about emotional reaction of the patient to pain;
   generating a plurality of signal metrics from the received information;
   calculating a score indicative of patient emotional reaction to pain using the generated plurality of signal metrics; and
   initiating or adjusting a neuromodulation therapy based at least in part on the calculated score.

2. The method of claim 1, wherein the neuromodulation therapy includes at least one of a spinal cord stimulation therapy, a deep brain stimulation therapy, a peripheral nerve stimulation therapy, a functional electrical stimulation therapy, a motor cortex stimulation therapy, a sacral nerve stimulation therapy, a radiofrequency ablation therapy, or a vagus nerve stimulation therapy.

3. The method of claim 1, wherein the received information about emotional reaction to pain includes information about facial, vocal, or behavioral expressions of the patient related to pain,
   wherein the neuromodulation therapy is delivered to a neural target for pain management.

4. The method of claim 3, comprising:
   trending at least one of the plurality of signal metrics over time;
   determining a rate of change in the trended at least one signal metric; and
   generating a diagnostic of a chronic pain or an abrupt pain based at least in part on the rate of change in the trended at least one signal metric.

5. The method of claim 4, wherein initiating or adjusting the neuromodulation therapy is further based on the generated diagnostic.

6. The method of claim 1, wherein the received information about emotional reaction to pain includes motor activity information indicative of or correlated to an emotional or psychological state of the patient.

7. The method of claim 6, wherein the received motor activity information is indicative of or correlated to an emotional or psychological reaction to pain.

8. The method of claim 6, wherein the motor activity information includes a speech motor control signal, and wherein the plurality of signal metrics generated from the received motor activity information includes one or more of speed, volume, pitch, inclination, regularity, or a degree of coordination during speech.

9. The method of claim 1, wherein the received information about emotional reaction to pain includes a facial image or video of the patient, and wherein the plurality of signal metrics include one or more facial image features.

10. The method of claim 9, wherein the one or more facial image features include at least one of a spatial or temporal change or a rate of change of a facial landmark.

11. The method of claim 1, wherein calculating the score indicative of patient emotional reaction to pain includes:
    calculating metric-specific scores respectively for each of the plurality of signal metrics; and
    determining a composite score using a weighted combination of the plurality of signal metrics each scaled by respective weight factors.

12. A non-transitory machine-readable storage medium that includes instructions that, when executed by one or more processors of a machine, cause the machine to perform operations comprising:
    receiving information about emotional reaction of a patient to pain;
    generating a plurality of signal metrics from the received information;
    calculating a score indicative of patient emotional reaction to pain using the generated plurality of signal metrics; and
    generating a control signal to initiate or adjust a neuromodulation therapy based at least in part on the calculated score.

13. The non-transitory machine-readable storage medium of claim 12, wherein the control signal to initiate or adjust the neuromodulation therapy includes directing the neuromodulation therapy to a neural target for pain management.

14. The non-transitory machine-readable storage medium of claim 12, wherein the instructions cause the machine to perform operations further comprising:
    trending at least one of the plurality of signal metrics over time;
    determining a rate of change in the trended at least one signal metric; and
    generating a diagnostic of a chronic pain or an abrupt pain based at least in part on the rate of change in the trended at least one signal metric.

15. The non-transitory machine-readable storage medium of claim 12, wherein the received information about emotional reaction to pain includes information about facial, vocal, or behavioral expressions of the patient related to pain,
    wherein the operation of calculating the score indicative of patient emotional reaction to pain includes calculating metric-specific scores respectively for each of the plurality of signal metrics, and determining a composite emotional reaction score using a weighted combination of the plurality of signal metrics each scaled by respective weight factors.

16. A medical-device system, comprising:
a therapy circuit configured to provide a neuromodulation therapy to a patient;
a receiver circuit configured to receive information about emotional reaction of the patient to pain; and
a controller circuit configured to:
generate a plurality of signal metrics from the received information;
calculate a score indicative of patient emotional reaction to pain using the generated plurality of signal metrics; and
generate a control signal to the therapy circuit to initiate or adjust the neuromodulation therapy based at least in part on the calculated score.

17. The medical-device system of claim 16, wherein the therapy circuit is configured to provide the neuromodulation therapy including at least one of a spinal cord stimulation therapy, a deep brain stimulation therapy, a peripheral nerve stimulation therapy, a functional electrical stimulation therapy, a motor cortex stimulation therapy, a sacral nerve stimulation therapy, a radiofrequency ablation therapy, or a vagus nerve stimulation therapy.

18. The medical-device system of claim 16, wherein the therapy circuit is configured to deliver the neuromodulation therapy to a neural target for pain management.

19. The medical-device system of claim 16, wherein the control circuit is configured to:
trend at least one of the plurality of signal metrics over time;
determine a rate of change in the trended at least one signal metric; and
generate a diagnostic of a chronic pain or an abrupt pain based at least in part on the rate of change in the trended at least one signal metric.

20. The medical-device system of claim 16, wherein the received information about emotional reaction to pain includes information about facial, vocal, or behavioral expressions of the patient related to pain,
wherein to calculate the score indicative of patient emotional reaction to pain, the controller circuit is configured to:
calculate metric-specific scores respectively for each of the plurality of signal metrics; and
determining a composite score using a weighted combination of the plurality of signal metrics each scaled by respective weight factors.

* * * * *